(12) United States Patent
Krag

(10) Patent No.: US 6,363,940 B1
(45) Date of Patent: Apr. 2, 2002

(54) SYSTEM AND METHOD FOR BRACKETING AND REMOVING TISSUE

(75) Inventor: David N. Krag, Shelburne, VT (US)

(73) Assignee: Calypso Medical Technologies, Inc., Seattle, WA (US)

(*) Notice: Subject to any disclaimer, the term of this patent is extended or adjusted under 35 U.S.C. 154(b) by 0 days.

(21) Appl. No.: 09/078,982

(22) Filed: May 14, 1998

(51) Int. Cl.$^7$ .............................................. A61B 19/00

(52) U.S. Cl. ...................... 128/899; 600/420; 600/431; 606/184

(58) Field of Search ................................ 600/431, 420, 600/458, 424; 606/1, 167, 170, 184; 128/899, 903

(56) References Cited

U.S. PATENT DOCUMENTS

| | | | |
|---|---|---|---|
| 4,114,601 A | * | 9/1978 | Abels |
| 4,222,374 A | * | 9/1980 | Sampson et al. |
| 4,395,910 A | | 8/1983 | Thomenius |
| 4,466,075 A | | 8/1984 | Groch et al. |
| 4,618,978 A | | 10/1986 | Cosman ..................... 378/164 |
| 5,050,608 A | | 9/1991 | Watanabe et al. |
| 5,099,845 A | * | 3/1992 | Besz et al. ................... 128/899 |
| 5,107,862 A | * | 4/1992 | Fabian et al. ............... 128/899 |
| 5,170,055 A | | 12/1992 | Carroll et al. |
| 5,197,466 A | | 3/1993 | Marchosky et al. ........ 128/399 |
| 5,198,877 A | | 3/1993 | Schulz |
| 5,205,289 A | | 4/1993 | Hardy et al. ............. 128/653.1 |
| 5,211,164 A | | 5/1993 | Allen ....................... 128/653.1 |
| 5,221,269 A | | 6/1993 | Miller et al. |

(List continued on next page.)

FOREIGN PATENT DOCUMENTS

| | | | |
|---|---|---|---|
| EP | 0 719 420 B1 | | 7/1996 |
| FR | 2635259 | * | 2/1990 |
| WO | WO 96/08208 | | 3/1996 |
| WO | WO 9608208 A1 | | 3/1996 |
| WO | WO 97/36192 | | 10/1997 |
| WO | WO 97/48438 | | 12/1997 |
| WO | WO 99/13775 | | 3/1999 |
| WO | WO 99/17133 | | 4/1999 |
| WO | WO 99/30182 | | 6/1999 |
| WO | WO 99/44506 | | 9/1999 |
| WO | WO 99/58055 | | 11/1999 |
| WO | WO 00/12009 | | 3/2000 |
| WO | WO 00/24332 | | 5/2000 |
| WO | WO 00/51514 | | 9/2000 |

OTHER PUBLICATIONS

Image–Guided Breast Biopsy: The ABBI* System, by William E. Kelley, M.D., 1997 www.ussurg.com/health–care/procedures/abbi.

The World's Most Versatile Biopsy System Offered Only by USSC, ABBI* System Features, 1997, www.ussurg.com/health–care/procedures/abbi.

Primary Examiner—Michael H. Thaler
(74) Attorney, Agent, or Firm—Perkins Coie LLP

(57) ABSTRACT

A system and method for bracketing a tissue volume (22) and later locating the bracketed tissue volume. The system includes a plurality of markers (30) and a probe (32) and detector (34) for use in locating the markers by providing information usable by a surgeon that is representative of changes in proximity between the probe and the plurality of markers. The markers have various detection characteristics, e.g., they transmit gamma rays, that are detectable by an associated probe and detector. The tissue volume is removed by manipulating a cutting tool based on the proximity information provided by the detector which can be used by the surgeon to define the boundary of the tissue volume. A two-part cutting tool (200) is provided for removing the tissue volume, and a tissue anchor (300) is provided for stabilizing the tissue during removal. The system and method of the invention are particularly useful in bracketing and then removing a tissue volume from amorphous, pliable tissue such as breast tissue.

26 Claims, 11 Drawing Sheets

U.S. PATENT DOCUMENTS

| | | | |
|---|---|---|---|
| 5,230,338 A | 7/1993 | Allen et al. ................ 128/653 | |
| 5,240,011 A | 8/1993 | Assa | |
| 5,246,005 A | 9/1993 | Carroll et al. | |
| 5,262,772 A | 11/1993 | Urbas et al. ........... 340/825.54 | |
| 5,325,873 A * | 7/1994 | Hirschi et al. ............... 128/899 | |
| 5,397,329 A | 3/1995 | Allen | |
| 5,417,210 A | 5/1995 | Funda et al. | |
| 5,425,367 A * | 6/1995 | Shapiro et al. | |
| 5,425,382 A | 6/1995 | Golden et al. | |
| 5,446,548 A | 8/1995 | Gerig et al. | |
| 5,515,853 A | 5/1996 | Smith et al. | |
| 5,526,812 A | 6/1996 | Dumoulin et al. | |
| 5,546,951 A | 8/1996 | Ben-Haim | |
| 5,568,809 A | 10/1996 | Ben-haim | |
| 5,572,999 A | 11/1996 | Funda et al. | |
| 5,617,857 A | 4/1997 | Chader et al. | |
| 5,622,170 A | 4/1997 | Schulz | |
| 5,622,187 A | 4/1997 | Carol | |
| 5,630,431 A | 5/1997 | Taylor | |
| 5,697,384 A * | 12/1997 | Miyawaki et al. .......... 128/899 | |
| 5,724,030 A | 3/1998 | Urbas et al. ........... 340/870.17 | |
| RE35,816 E | 6/1998 | Schulz | |
| 5,779,638 A | 7/1998 | Vesely et al. | |
| 5,782,775 A | 7/1998 | Milliman et al. | |
| 5,797,849 A | 8/1998 | Vesely et al. | |
| 5,817,022 A | 10/1998 | Vesely | |
| 5,828,770 A | 10/1998 | Leis et al. | |
| 5,830,144 A | 11/1998 | Vesely | |
| 5,868,673 A | 2/1999 | Vesely | |
| 5,868,675 A | 2/1999 | Henrion et al. | |
| 5,879,297 A * | 3/1999 | Haynor et al. .............. 600/424 | |
| 5,879,357 A | 3/1999 | Heaton et al. | |
| 5,902,238 A | 5/1999 | Golden et al. | |
| 5,902,310 A | 5/1999 | Foerster et al. ............. 606/142 | |
| 5,907,395 A | 5/1999 | Schulz et al. | |
| 5,923,417 A | 7/1999 | Leis | |
| 5,951,481 A | 9/1999 | Evans | |
| 5,987,349 A | 11/1999 | Schulz | |
| 6,026,818 A * | 2/2000 | Blair et al. ................. 128/899 | |
| 6,061,644 A | 5/2000 | Leis | |
| 6,094,007 A | 7/2000 | Faul et al. | |
| 6,129,658 A | 10/2000 | Delfino et al. | |
| 6,173,715 B1 | 1/2001 | Sinanan et al. | |

\* cited by examiner

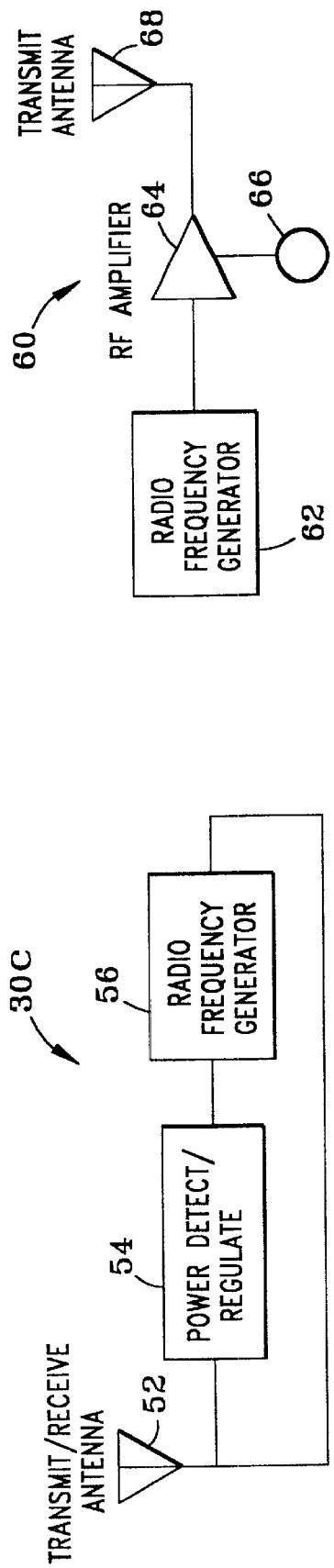
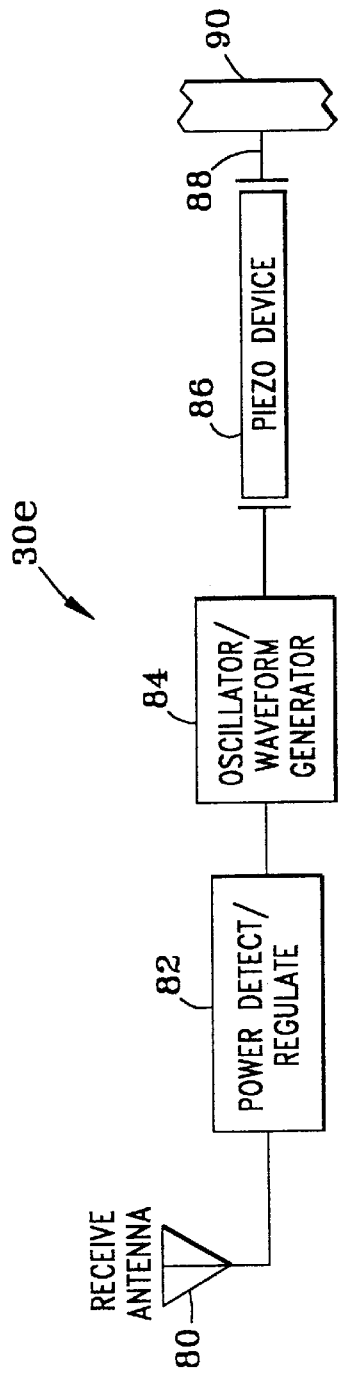
FIG. 3a
FIG. 3b
FIG. 4

SYSTEM AND METHOD FOR BRACKETING AND REMOVING TISSUE

FIELD OF THE INVENTION

The present invention relates to a system for and method of bracketing a tissue volume containing a tissue mass, e.g., a non-palpable breast tumor, using markers to define the boundary of the tissue volume and a probe and detector to locate the markers. The present invention also pertains to a method of removing the bracketed tissue, a circular cutting tool for removing tissue in connection with this and other methods, and a tissue anchor for reducing mobility of tissue during tissue removal procedures.

BACKGROUND OF THE INVENTION

A current technique for performing an excisional biopsy of a non-palpable breast lesion that has been identified by mammogram or other method involves placement of a needle or guide wire (e.g., a "Kopanz wire"), with or without blue dye, to guide the surgeon to the lesion. The tip of the needle is generally placed directly in or as close as possible to the lesion. When larger or more complex lesions are encountered, two or more guide wires are sometimes placed at each edge of the lesion. The entry point of the needle through the skin of the breast is usually several centimeters from the lesion due to the logistics of needle placement. The surgeon does not cut along the shaft of the needle from the skin because the distance is too great. Instead, the surgeon must estimate where in the breast the lesion is located by making reference to the location of the needle.

This technique is not optimal. Due to the amorphous and highly pliable nature of certain tissue, e.g., breast tissue, it can be difficult to properly define the margins of tissue to be removed, both during and after insertion of the needle(s). Also, it is often difficult for the surgeon to detect the exact depth of the lesion based on the placement of the needles. For these reasons it is not uncommon that the biopsied tissue does not contain the mammographically positive specimen. In other cases, as a result of the difficulty of estimating the proper location of the boundaries of the volume of tissue to be removed, the lesion ends up being eccentrically positioned within the volume of tissue excised. This calls into question the adequacy of the margin of normal tissue surrounding the lesion. In still other cases, more normal tissue is removed than is required, which is disadvantageous in this era of tissue-conserving therapies.

In other fields of surgery it is known to target portions of a human body using various devices, and then refer to such devices in connection with the removal or treatment of such portions. For example, U.S. Pat. No. 5,630,431 to Taylor (the "'431 patent") describes a surgical manipulator that is controlled, in part, by information received from beacons that are positioned proximate to a region of a human body to be treated. As another example, U.S. Pat. No. 5,397,329 to Allen (the "'329 patent") describes fiducial implants for a human body that are detectable by an imaging system. The fiducial implants are implanted beneath the skin and are spaced sufficiently from one another to define a plane that is detectable by the imaging system and is used in connection with creation of images of a body portion of interest. These images are then used, for instance, in eliminating a tumor by laser beam.

Unfortunately, the devices described in the '431 and '329 patents are vastly more complex, and hence expensive, than is appropriate for many surgical procedures, particularly with the emphasis on cost containment in managed health care. Furthermore, due to the amorphous, pliable nature of certain tissue, the systems of the '431 and '329 patents cannot be used effectively. Systems of the type described in the '431 and '329 patents require that the devices (e.g., beacons or fiducial implants) defining the body portions of interest be substantially fixed relative to one another and relative to such body portions. These systems generally function effectively when the devices defining the body portion of interest are inserted in bone, e.g., in a skull in connection with brain surgery or treatment, but are not believed to operate as intended when the devices are inserted in amorphous, pliable tissue.

Breast lesions are typically excised with a scalpel manipulated directly by the surgeon. With the current emphasis on breast conserving surgical therapies, the above-described procedure for removing a breast lesion is typically performed through a narrow opening in the skin created by slitting and then pulling apart the skin. It tends to be difficult to manipulate the scalpel within this opening so as to remove the desired volume of tissue. The amorphous, pliable nature of breast tissue exacerbates removal of such tissue inasmuch as application of force to the scalpel causes movement of the breast tissue relative to the opening in the skin.

Circular cutting tools are not widely used in surgery. Recently, however, United States Surgical Corporation of Norwalk, Connecticut, introduced a relatively small diameter, e.g., 5–20 mm, circular cutting tool identified by the trademark ABBI for removing a cylinder of breast tissue for biopsy purposes. The ABBI tool includes an oscillating, motorized, circular cutting blade that incises the breast tissue. While use of the ABBI tool is believed to be a relatively effective way to perform a core biopsys of breast tissue, it is not apparently designed to remove cylinders of tissue having a diameter much in excess of about 20mm. As such, it is not adapted for use in surgeries involving the removal of relatively large tissue portions in a single cutting sequence. In addition, the ABBI tool's effectiveness in therapeutic, rather than diagnostic, surgeries has not been confirmed.

Detectors are used to locate organs or other portions of the body that have taken up a radioactive material, e.g., an antibody labeled with a radioactive material. For example, the gamma ray probe described in U.S. Pat. Nos. 5,170,055 and 5,246,005, both to Carroll et al., and sold by Care Wise Medical Products Corporation, Morgan Hill, California, and identified by the trademark C-TRAK, provides an audio output signal, the pitch of which varies with changes in relative proximity between the probe and a body portion that has taken up an antibody labeled with a gamma ray producing material, e.g., technetium 99. Once the body portion is detected, it is removed by known surgical techniques.

Even with the systems and techniques described above, it remains difficult for a surgeon to remove a tissue mass in amorphous, pliable tissue, such as breast tissue, so as to ensure the entire tissue mass is removed while at the same time removing only minimal portions of adjacent tissue. As a result, more unaffected tissue surrounding the targeted tissue mass is typically removed than is desired.

SUMMARY OF THE INVENTION

One aspect of the present invention is a system for bracketing a tissue volume. The system includes a plurality of markers, each of which has a maximum dimension of no more than 5 mm, as measured along any axis extending through the marker. In addition, the system includes a probe and a detector connected to the probe that provides information when the probe is proximate to one of the plurality of markers.

Another aspect of the present invention is a surgical marker that includes a quantity of colored dye and a capsule encasing the quantity of colored dye. One or both of the dye and capsule are readily imagable by at least one of ultrasonic, magnetic resonance and X-ray energy.

Yet another aspect of the present invention is a cutting tool that includes a first portion and a second portion. The first portion includes a first blade having a first edge with a first curved configuration and a first connector. The second portion includes a second blade having a second edge. The second edge has a second curved configuration that is designed so that when the second blade is positioned in operative engagement with the first blade, the first edge and the second edge form a substantially continuous cutting edge. In addition the second portion includes a second connector positioned and designed to releasably engage the first connector so as to releasably secure the first and second blades in operative engagement.

Still another aspect of the present invention is a tissue anchor for reducing mobility of tissue during surgical or other procedures. The tissue anchor includes an elongate tube having a central bore, a distal end and a proximal end. The tube comprises at least one aperture adjacent the distal end. The tissue anchor also has an elongate member with a portion sized for receipt and axial movement in the central bore between a first position and a second position. The portion has a distal end and the elongate member includes at least one anchor member attached to the portion adjacent the distal end. In addition, the at least one anchor member is sized and positioned so that when the portion is in the first position the at least one anchor member is at least partially received in the elongate tube and when the portion is in the second position the at least one anchor member projects through the at least one aperture.

Yet another aspect of the present invention is a method of removing a tissue volume from a tissue portion using a plurality of markers. The method comprising the steps of (i) positioning a plurality of markers so as to define a boundary of the tissue volume, (ii) detecting the location of a first one of the plurality of markers, and (iii) incising portions of the tissue portion adjacent the first one of the plurality of markers substantially along the boundary adjacent the location.

Still another aspect of the present invention is a method of bracketing a tissue mass in a piece of tissue using a plurality of markers. The method comprising the steps: (i) generating an image of the tissue mass, and (ii) referring to the image of the tissue mass, positioning the plurality of markers in the piece of tissue so as to define a boundary of a tissue volume that includes the tissue mass.

Other aspects of the invention are described in the following detailed description of the invention, in the claims and in the accompanying drawings.

BRIEF DESCRIPTION OF THE DRAWINGS

FIG. 3a is a block diagram of the elements of one embodiment of the marker illustrated in FIG. 2c;

FIG. 3b is a block diagram of the RF exciter used with the marker illustrated in FIG. 3a;

FIG. 4 is a block diagram of the elements of one embodiment of the marker illustrated in FIG. 2e;

DETAILED DESCRIPTION OF THE INVENTION

Figure 1:
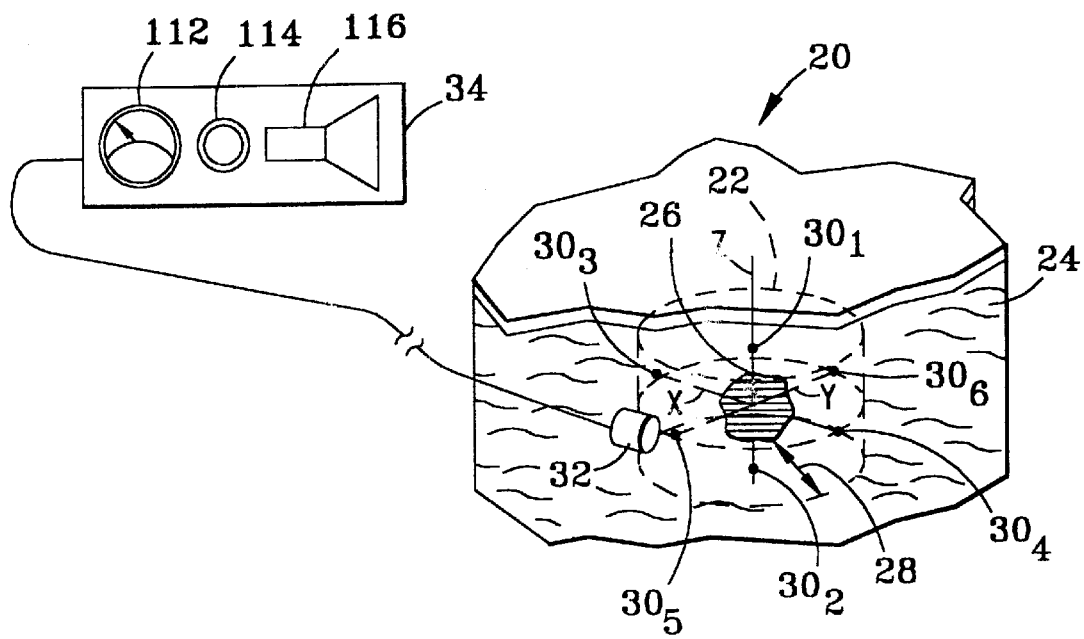
FIG. 1 is an idealized perspective view of a tissue mass and surrounding tissue volume that is bracketed by the markers of the present invention, with two markers being positioned on opposite ends of each of mutually orthogonal X, Y and Z axes intersecting the tissue mass so as to define the boundary of the tissue volume, and with the probe and detector of the present invention being positioned adjacent the tissue volume.

Referring to FIG. 1, the present invention is a system 20 for defining the boundaries of, i.e., bracketing, a tissue volume 22 in a tissue portion 24. Typically, tissue volume 22 will include a tissue mass 26, e.g., a breast lesion, that is targeted for removal and a tissue margin 28 of unaffected tissue surrounding the tissue mass. After tissue volume 22 is bracketed, system 20 can be used to locate the defined boundaries of the tissue volume, e.g., in connection with the surgical removal of tissue mass 26.

As described in more detail below, the present invention is also directed to a method of bracketing tissue volume 22 using system 20, and a method of removing tissue volume 22 using system 20. These methods can be advantageously, although not necessarily, accomplished with other aspects of the present invention, i.e., cutting tool 200 (FIGS. 9 and 10) and tissue anchor 300 (FIGS. 11–13), both described below.

System 20 comprises a plurality of markers 30, a probe 32 and a detector 34 connected to the probe. As described in more detail below, markers 30 are implanted in tissue portion 24 under the guidance of a conventional imaging system not forming part of the present invention, so as to bracket tissue volume 22. Such imaging systems may include ultrasound, magnetic resonance imaging ("MRI"), computer-aided tomography ("CAT") scan, and X-ray systems. Markers 30 are imagable with the imaging energy generated by the imaging system. For example, if an ultrasound imaging system is used to implant markers 30, the latter are configured and made from a material that strongly reflects ultrasound energy. Materials that are imagable with the energy generated by such systems are well known to those skilled in the art, and so are not described in detail here. Following implantation of markers 30, probe 32 and detector 34 are used to locate the markers, as described in more detail below.

The terms "probe 32" and "detector 34" are used generically herein to refer to all embodiments of the probe and detector described below. Specific embodiments of the probe 32 and detector 34 are identified using a prime notation described below, i.e., probe 32' or detector 34".

Markers

Preferably, markers 30 are biologically inert and are relatively small so that they interfere as little as possible with the removal or other treatment of tissue volume 22. Markers 30 may have different geometric configurations, e.g., spherical, disk-like, cylindrical. However, it is preferred that the greatest dimension of a marker 30, as measured along any axis extending through the marker from one surface to an opposite surface, is not more than about 5 mm. Ideally, markers 30 are even smaller, i.e., the greatest dimension is about 1–2 mm.

Figure 2A:
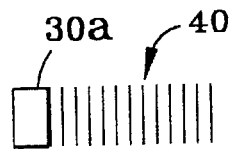
FIGS. 2a–2g are schematic representations of various embodiments of the markers of the present invention and their associated detection characteristics.

In addition, markers 30 each have a detection characteristic to enable detection by probe 32 and detector 34. The detection characteristics of the various embodiments of markers 30 can be characterized as active or passive. In the active category, the detection characteristic of a first embodiment of marker 30, illustrated in FIG. 2a as marker 30a, is gamma rays 40. In this regard, marker 30a may include materials such as technetium 99, cobalt isotopes or iodine isotopes. Such materials may be obtained from DuPont of Billerica, Mass. Preferably, each marker 30a generates gamma rays 40 having a field strength in the range of 1–100 microCurries.

Figure 2B:
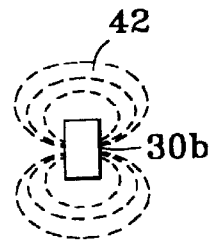

Also in the active category, in a second embodiment of marker 30, illustrated in FIG. 2b as marker 30b, the detection characteristic is magnetic field 42. Markers 30b of the second embodiment thus contain ferromagnetic materials in which a magnetic field can be induced, or alternatively are permanently magnetized and so have an associated permanent magnetic field. In FIG. 2b, magnetic field 42 represents both the induced and inherent magnetic fields. Strong permanent magnets, such as those made from Samarium-Cobalt, are typically preferred for markers 30b.

Figure 2C:
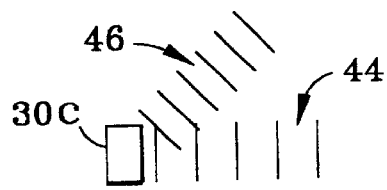

Referring to FIG. 2c, in a third embodiment, again in the active category, marker 30c emits radio frequency ("RF") signal 44 in response to a triggering signal 46. Various energy sources may be used for triggering signal 46, including a magnetic field, ultrasound or radio frequency energy. In this latter case, marker 30c is preferably designed to receive triggering signal 46 which has a first RF wavelength, and in response thereto, emit signal 44 of a second RF wavelength. In the simplest case, no data, other than the specific radio frequency itself, is carried in signal 44. Alternatively, markers 30c may all transmit signal 44 at a single frequency, with data uniquely identifying each marker being carried in signal 44 emitted by each marker.

A suitable marker 30c is illustrated in FIG. 3a. This marker 30c includes a transmit/receive antenna 52 for receiving an RF signal at a first frequency and transmitting an RF signal at a second frequency. Also included is a power detect/regulate circuit 54 connected to antenna 52 that detects the presence of, and regulates, the RF signal received by the antenna. The regulated RF signal is provided from circuit 54 to drive radio frequency generator 56 which generates an RF signal at a second frequency. As discussed in more detail below, when multiple markers 30c are used together in a given bracketing procedure, preferably each marker transmits RF signals at a second frequency which is unique to the marker. The RF signal generated by radio frequency generator 56 is then provided to antenna 52 where it is transmitted as an RF signal. While it is preferred the frequency of RF signal 44 transmitted from markers 30c be unique for each marker 30c used in a given bracketing procedure, the frequency of the received RF signal 46 is preferably common with respect to all of the markers 30c used in the bracketing procedure.

Referring to FIG. 3b, an RF exciter device 60 for generating RF signal 46 is illustrated. RF exciter 60 includes a radio frequency generator 62 for generating RF signal 46 at a predetermined frequency and an RF amplifier 64 for amplifying the output from the radio frequency generator. The sensitivity of amplifier 64 may be controlled using gain adjustment 62 coupled to the amplifier. The output of RF amplifier 64 is provided to transmit antenna 68 which transmits RF signal 46. Transmit antenna 68 of RF exciter 60 is preferably placed in relatively close proximity to marker 30c, with appropriate gain adjustment of RF amplifier 64 being achieved by control gain adjustment 66 until a suitable return signal is absorbed from detector 34", discussed below and illustrated in FIG. 8.

Figure 2D:
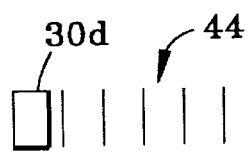

In a fourth embodiment, again in the active category, marker 30d, illustrated in FIG. 2d, continuously emits signal 44 at specific frequencies in the radio frequency spectrum. The marker 30c illustrated in FIG. 3a and described above can be satisfactorily employed as marker 30d by adding a battery (not shown) in place of power detector portion of circuit 54 of marker 30c. RF exciter 60 is not required in connection with marker 30d, insofar as the battery generates the energy used by the marker in producing RF signal 44.

Figure 2E:
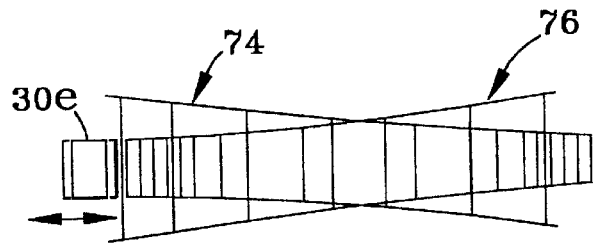

As a fifth embodiment in the active category, marker 30e, illustrated in FIG. 2e, is designed to vibrate following implantation. This vibration is a detection characteristic that is chosen to enhance image contrast when marker 30 is intended to be detected using a probe 32 and detector 34 that perform ultrasound imaging. More specifically, incoming ultrasound signal 74 is reflected off marker 30e as reflected ultrasound signal 76, with a Doppler shift component being added to the reflected signal due to the vibration of the marker to enhance imagability of the marker. The vibration frequency of marker 30e will vary depending upon the frequency of ultrasound energy generated by probe 32, but is preferably lower than the frequency of incoming ultrasound signal 74 which is typically 7.5 MHz, i.e., the vibration frequency is preferably in the 50 Hz to 50 KHz range.

A suitable marker 30e that achieves the functionality described above is illustrated in FIG. 4. This marker 30e includes an antenna 80 for receiving an RF signal that provides the energy driving the marker. A power detection and regulation circuit 82 is connected to antenna 80 for detecting when the antenna is receiving an RF signal and for regulating the signal for use by oscillator and waveform generator circuit 84 connected to circuit 82. Circuit 84 converts the regulated RF signal received from circuit 82 into an oscillating electrical signal, preferably in the audio frequency range (i.e., 20 Hz–20 kHz), having a waveform that is optimized to drive piezo-electric device 86 connected to circuit 84. Piezo-electric device 86 is a conventional piezo-electric device of the type that converts an oscillating electrical input signal into mechanical oscillations. Piezo-electric device 86 is attached via support 88 to outer housing 90 of marker 30e. Housing 90 is designed to resonate at the mechanical oscillation frequency of piezo-electric device 86.

Figure 5:
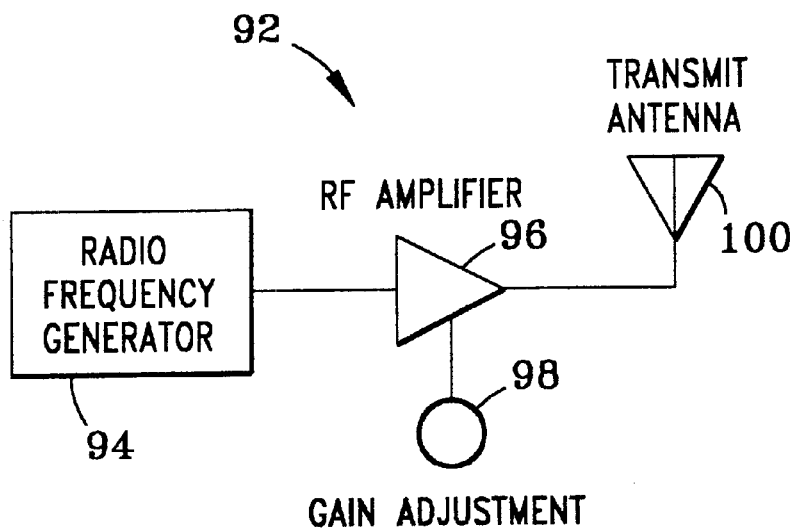
FIG. 5 is a block diagram of the RF exciter used with the marker illustrated in FIG. 4.

Referring to FIG. 5, an RF coupled acoustic exciter 92 is provided for generating the RF signal received by antenna 80 of marker 30e. Exciter 92 includes a radio frequency generator 94 for generating an RF signal. RF amp 96, with a gain adjustment 98 connected thereto, is provided for receiving and amplifying the output signal from generator 94. A transmit antenna 100 is provided for receiving the output of amp 96 and transmitting the RF signal used to drive marker 30e. In use, gain 98 of amp 96 is adjusted to amplify the RF signal produced by generator 94 such that marker 30e is caused to mechanically oscillate so it is most clearly observable by the ultrasound imaging system (not shown) used in conjunction with marker 30e.

As those skilled in the art will appreciate, other circuit configurations may be used in marker 30e to cause piezo-electric device 86 to vibrate. For example, a frequency divider circuit (not shown) may be used in place of oscillator/waveform generator circuit 84. With such alternative, exciter 92 is modified to include a variable frequency oscillator (not shown) in place of radio frequency generator 94.

Figure 2F:
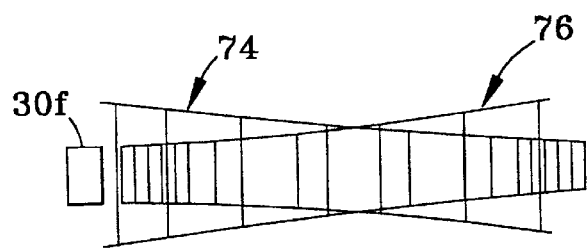

In the passive category, the detection characteristic in a sixth embodiment of marker 30, illustrated as marker 30f in FIG. 2f, is opacity to incoming ultrasound signal 74. That is, marker 30f reflects incoming sound energy sufficiently to create a strong image in reflected signal 76 so as to enhance imagability using a conventional ultrasound imaging system. In many cases, it will be advantageous to incorporate the detection characteristics of marker 30f in marker 30e.

Figure 6:
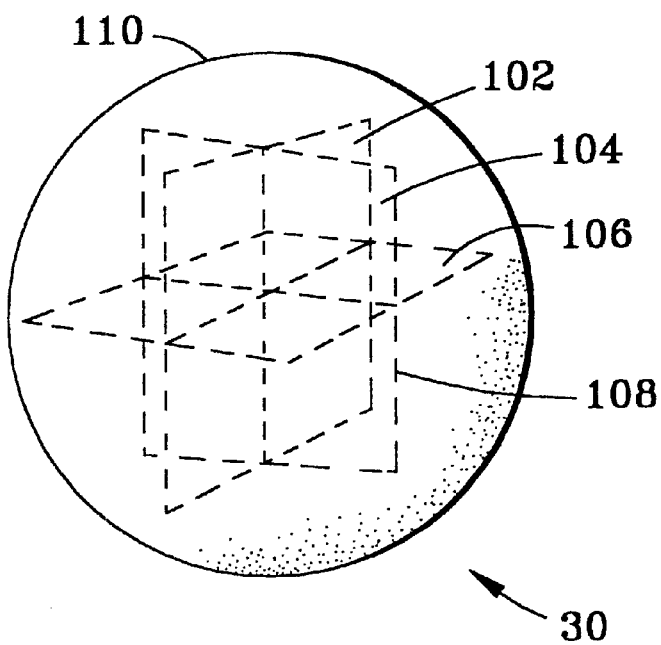
FIG. 6 is a perspective view of one embodiment of the marker illustrated in FIG. 2f, with details of internal construction being illustrated in phantom view.

While those skilled in the art are familiar with materials and configurations that can be used for marker 30f, one suitable marker 30f is illustrated in FIG. 6. This marker 30f includes plate 102, plate 104 and plate 106, all of which are preferably arranged in mutually orthogonal relationship. It is preferred that each of the plates 102–106 has a square configuration and the length of each edge of the plates, e.g., the length of edge 108 of plate 104, is preferably about twice the wavelength of incoming ultrasound signal 74. For example, when incoming ultrasound signal 74 has a wavelength of 7.5 MHz, edge 108 has a length of about 2 mm. Plates 102–106 are made from a material that strongly reflects ultrasound energy, e.g., aluminum, and typically have a thickness in the range of 10–100 μm. Plates 102–106 ideally are enclosed in a biologically non-reactive casing 110. The latter is preferably made from a material that does not have strong ultrasound reflection characteristics, e.g., a soft polymer.

Figure 2G:
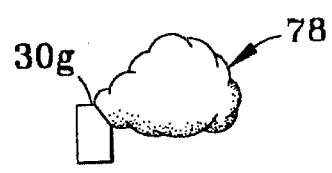

Also in the passive category, marker 30g of the seventh embodiment, illustrated in FIG. 2g, comprises a capsule (not shown) filled with a colored dye 78, e.g., a vital dye. Either or both the capsule and dye 78 of marker 30g are made from a material that is imagable by the imaging system, e.g., ultrasound, used to implant the markers, as described in more detail below. The capsule is made from gelatin or other suitable material that is selected to be sufficiently tough to withstand insertion into tissue volume 22, but is relatively easily cut by the cutting tool used to remove the tissue volume, e.g., a conventional surgical scalpel or cutting tool 200 described below. Marker 30g provides a visual guide as to its location by releasing colored dye 78 when severed by a surgical cutting tool. In this regard, probe 32 and detector 34 are not used in connection with marker 30g.

Markers 30a, 30b and 30f may be made from a solid structure containing material having the desired detection characteristic. Alternatively, markers 30a, 30b and 30f may be made from a capsule filled with a dye, such as is used for marker 30g, containing material having the desired detection characteristic. As another alternative, all embodiments of markers 30 may include a dye contained in an outer capsule having the requisite toughness and severability characteristics noted above.

Probe and Detector

The design and function of probe 32 and detector 34 depend upon the embodiment of marker 30 used. However, for all embodiments of marker 30 (except marker 30g), detector 34 is designed to provide humanly recognizable information when probe 32 is positioned within a selected proximity, e.g., 1–5 cm, of a given marker. This information may take one of a variety of forms, including a burst of humanly perceivable sound, constant or intermittent illumination of a light, movement of a needle on a dial, a short burst of air, change of data in a visual display, increased image brightness or contrast (in the case when detector 34 is an ultrasound imaging system, as discussed below) or other humanly perceivable proximity information. In this regard detector 34 may include a dial 112, light 114, speaker 116, or other appropriate devices for generating the selected form of humanly perceivable information.

Preferably, although not necessarily, detector 34 provides humanly recognizable information that indicates changes in proximity of probe 32 to a given marker 30. Thus, rather than merely providing static or threshold information that probe 32 is within a predetermined range of a given marker 30, detector 34 preferably provides proximity information having an attribute or characteristic that varies as a function of changes in proximity of the probe relative to the marker. For example, if the proximity information is sound, the pitch is varied with changes in proximity. Or, as another example, if the proximity information is light, the brightness of the light changes with changes in proximity.

A probe and detector that may be satisfactorily employed as probe 32 and detector 34, respectively, when the latter is intended to detect maker 30a, is sold by Care Wise Medical Products Corporation of Morgan Hill, Calif. and is identified by the trademark C-TRAK.

Figure 7:
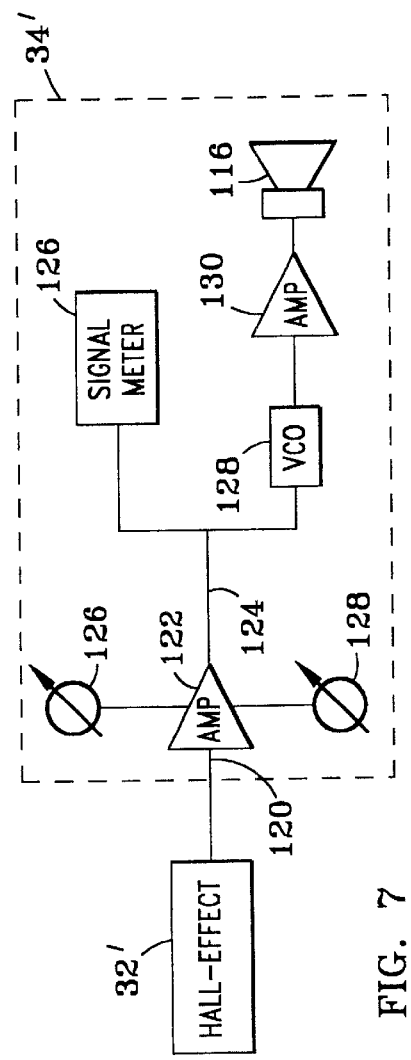
FIG. 7 is a block diagram of the probe and detector used with the marker illustrated in FIG. 2b.

The C-TRAK probe, which is described in U.S. Pat. Nos. 5,170,055 and 5,246,005 to Carroll et al., which are incorporated herein by reference, provides a humanly audible sound, the pitch of which varies with changes in proximity of the probe to tissue labeled with gamma ray producing material. Referring to FIGS. 1, 2b and 7, when probe 32 and detector 34 are intended for use in detecting marker 30b, which generates a magnetic field 42, probe 32' and detector 34' illustrated in FIG. 7 may be satisfactorily employed. Probe 32' includes a conventional Hall effect sensor (not shown) that provides an output signal on line 120, the voltage of which varies as a function of proximity of the probe to the magnetic field generated by a marker 30b. Detector 34' is connected to probe 32' via line 120, and includes an amplifier 122 connected to line 120 for amplifying the signal from the Hall effect sensor in probe 32'. Amplifier 122 includes an offset adjustment 126 and a gain adjustment 128. Offset adjustment 126 is provided to cancel the effects of any ambient magnetic fields, such as that of the earth. Gain adjustment 128 is provided to control the overall sensitivity of detector 34'. The amplified signal from amplifier 122 is delivered on line 124 to signal meter 126, which may comprise a dial with a movable needle, an LED or other device for representing signal strength. Also connected to line 124 is voltage controlled oscillator 128, the output of which is provided to amplifier 130. The output of amplifier 130 drives speaker 116. The frequency of the output signal from voltage controlled oscillator 128 varies as function of changes in voltage of the signal delivered on line 124, which in turn causes the pitch of the sound produced by speaker 116 to vary as a function of changes in the voltage of the signal on line 124. As those of ordinary skill in the art will appreciate, other devices for providing humanly recognizable information representing changing proximity, e.g., a light may be employed instead of speaker 116.

Figure 8:
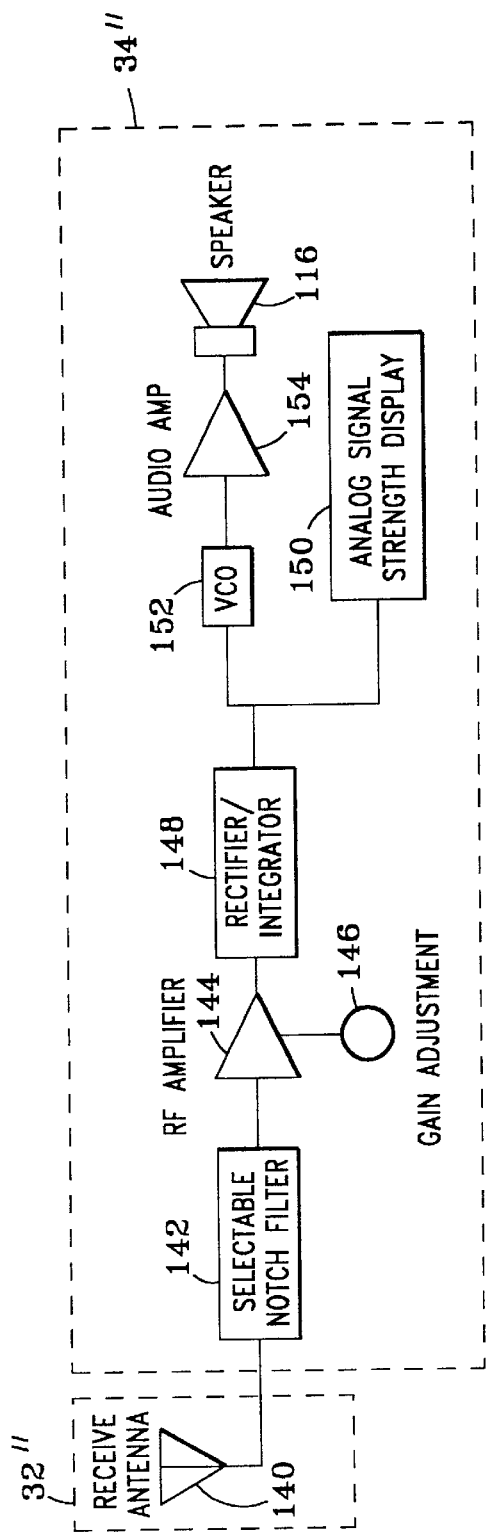
FIG. 8 is a block diagram of the probe and detector used with the marker illustrated in FIG. 2c.

Referring to FIGS. 1, 2c and 8, for markers 30c and 30d, which generate radio frequency energy, probe 32" and detector 34" are provided for use in detecting the markers. Probe 32" includes a conventional coil antenna 140 for receiving an RF signal. Detector 34" includes a selectable notch filter 142 connected to antenna 140 which permits tuning of the detector to the unique RF frequency of signal 44 emitted by markers 30c or 30d. A tuning knob or other user adjustable mechanism (neither shown) is attached to selectable notch filter 142 to permit a user to perform such tuning. The output of selectable notch filter 142 is provided to RF amplifier 144, the overall sensitivity of which may be controlled by gain adjustment 146 attached to the amplifier. The output of RF amplifier 144 is provided to rectifier/integrator circuit 148 which rectifies and time filters the signal. The output of rectifier/integrator circuit 148 is provided to analog signal strength display 150 which provides a visual indication of the proximity of probe 32" to marker 30c. In addition, the output of rectifier/integrator circuit 148 is provided to voltage oscillator 152 which generates an output signal, the frequency of which varies as a function of the voltage level of the signal provided by rectifier/integrator circuit 148. The output signal of the voltage control oscillator 152 is amplified by audio amplifier 154, which in turn drives speaker 116. Accordingly, the pitch of the sound generated by speaker 116 varies as a function of the strength of the RF signal received by probe 32", and hence as a function of the proximity of probe 32" to markers 30c or 30d.

A suitable probe 32 and detector 34 for use with the markers 30e and 30f is the ultrasound imaging system available from Dornier Surgical Products, Inc., Phoenix, Ariz., is identified by the name Performa, and generates ultrasound energy having a frequency of 7.5 MHZ.

Cutter

Figure 9:
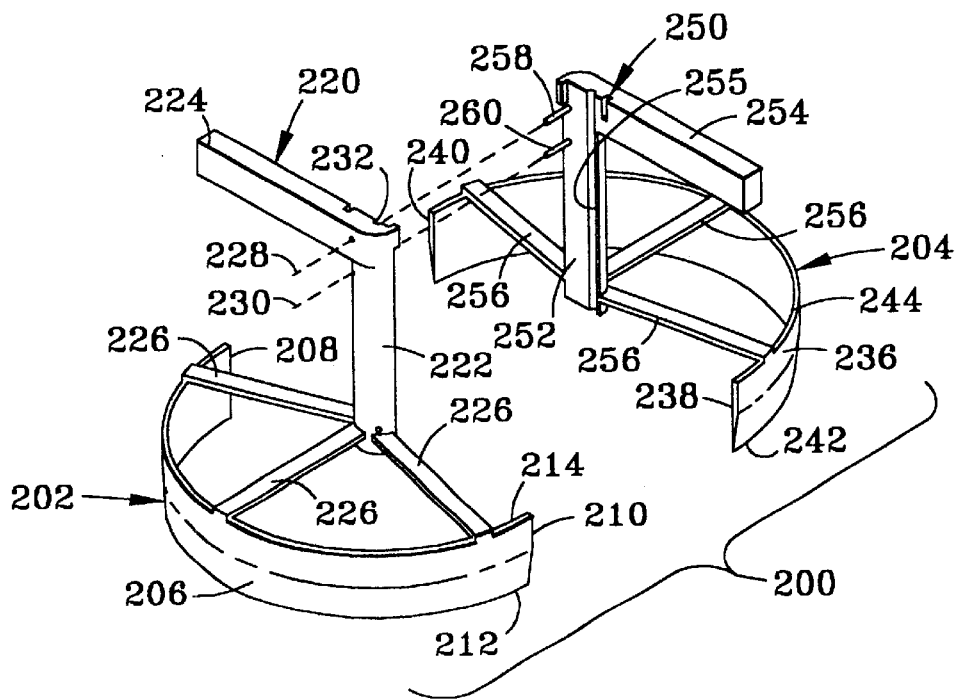
FIG. 9 is an exploded perspective view of the cutter of the present invention, with the two portions of the cutter being shown in disengaged, spaced relation.
Figure 10:
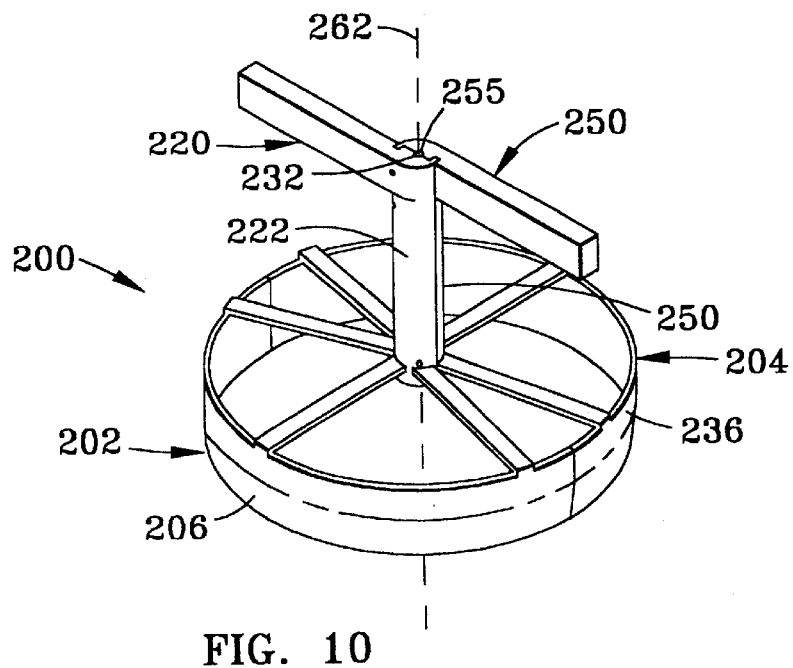
FIG. 10 is a perspective view of the cutter illustrated in FIG. 9, with the two portions of the cutter being shown in engaged, cooperative relation.

As described in more detail below in connection with the description of methods of using system 20, tissue volume 22 that is bracketed with markers 30 may be surgically removed using one of a variety of tools. Referring to FIGS. 9 and 10, one of these tools is cutter 200.

Cutter 200 includes portions 202 and 204. Portion 202 has a curved plate 206 that preferably traverses an arc of 180°, as measured between ends 208 and 210. Plate 206 includes a bottom edge 212 that is preferably sharpened. Plate 206 also includes a top edge 214 that is typically blunt.

Portion 202 also includes a handle 220 having an elongate central section 222 and a transverse section 224 attached to an upper end of the central section. Preferably, transverse section 224 extends normally to the long axis of central section 222, although other non-orthogonal relationships are encompassed by the present invention. Handle 220 is attached to curved plate 206 by several, e.g., three, spokes 226 that are attached to the plate at spaced locations and extend radially inwardly from the plate toward the bottom end of central section 222 where they are also attached. Handle 220 also includes apertures 228 and 230. As illustrated in FIGS. 9 and 10, apertures 228 and 230 are positioned at the upper end of handle 220. However, it is to be appreciated that apertures 228 and 230 may be positioned at other locations in central section, and, as an alternative one and more than two apertures may be used. Handle central section 222 also includes an elongate groove 232 extending the length of the central section.

Portion 204 is nearly identical to portion 202. In this regard, portion 204 includes a curved plate 236 that traverses an arc of 180° between ends 238 and 240, has a bottom edge 242 that is preferably sharpened, and has a top edge 244. Portion 204 also includes a handle 250 having a central section 252 and a transverse section 254, with central section 252 and curved plate 236 being connected by spokes 256. Handle central section 252 includes an elongate groove 255 extending the length of the central section. The placement of groove 255 on central section 252 is selected so that when portion 202 and 204 are positioned in operative engagement, as illustrated in FIG. 10 and described in more detail below, groove 255 confronts groove 232 in central section 222, and together the grooves form a central bore extending the length of central sections 222 and 252. The thickness of plate 236, as measured between edges 242 and 244, is preferably the same as the thickness of plate 236, as measured between edges 212 and 214. This thickness is typically in the range of 2 mm–25 mm.

Portion 204 differs from portion 202 in that it includes projections 258 and 260 in place of apertures 228 and 230. Projections 258 and 260 are sized and positioned to be snugly received in apertures 228 and 230, respectively, when portions 202 and 204 are positioned in operative engagement, as illustrated in FIG. 10. Transverse section 252 is preferably positioned relative to central section 250 so that when portions 202 and 204 are positioned in operative engagement, transverse section 252 extends in an opposite direction relative to transverse section 224.

When portions 202 and 204 are assembled to perform a cutting operation, they confront and engage one another, as illustrated in FIG. 10. In this regard, the radii of curvature of curved plates 206 and 236 are preferably substantially identical so that when end 210 contacts end 238 and end 208 contacts end 240, as illustrated in FIG. 10, plates 206 and 236 form a circular structure. In this engaged relationship, central sections 222 and 250 contact one another, with a central rotational axis 262 extending between the sections along their longitudinal axes. Also in this engaged relationship, apertures 228 and 230 receive projections 258 and 260, respectively, which ensures a rotational force applied about axis 262 to one of transverse sections 224 and 252 is transmitted from one of portions 202 and 204 to the other.

In certain applications it may be desirable to modify the construction of, or even eliminate, handles 220 and 250 from cutter 200. When so modified, it is preferred that connectors or other engagement mechanisms be provided for releasably securing portion 202 in operative engagement with portion 204, as illustrated in FIG. 10, so that both portions rotate together when a rotational force is applied to one of the portions, as described in more detail below in connection with the discussion of the operation of cutter 200. Such connectors or other engagement mechanisms may be provided at ends 208, 210, 240 and 242, where spokes 226 join and spokes 256 join, or at other appropriate locations.

Cutter 200 is preferably made from stainless steel. However, other materials including aluminum and certain plastics may be used in the construction of cutter 200.

Tissue Anchor

Figures 11, 12, 13:
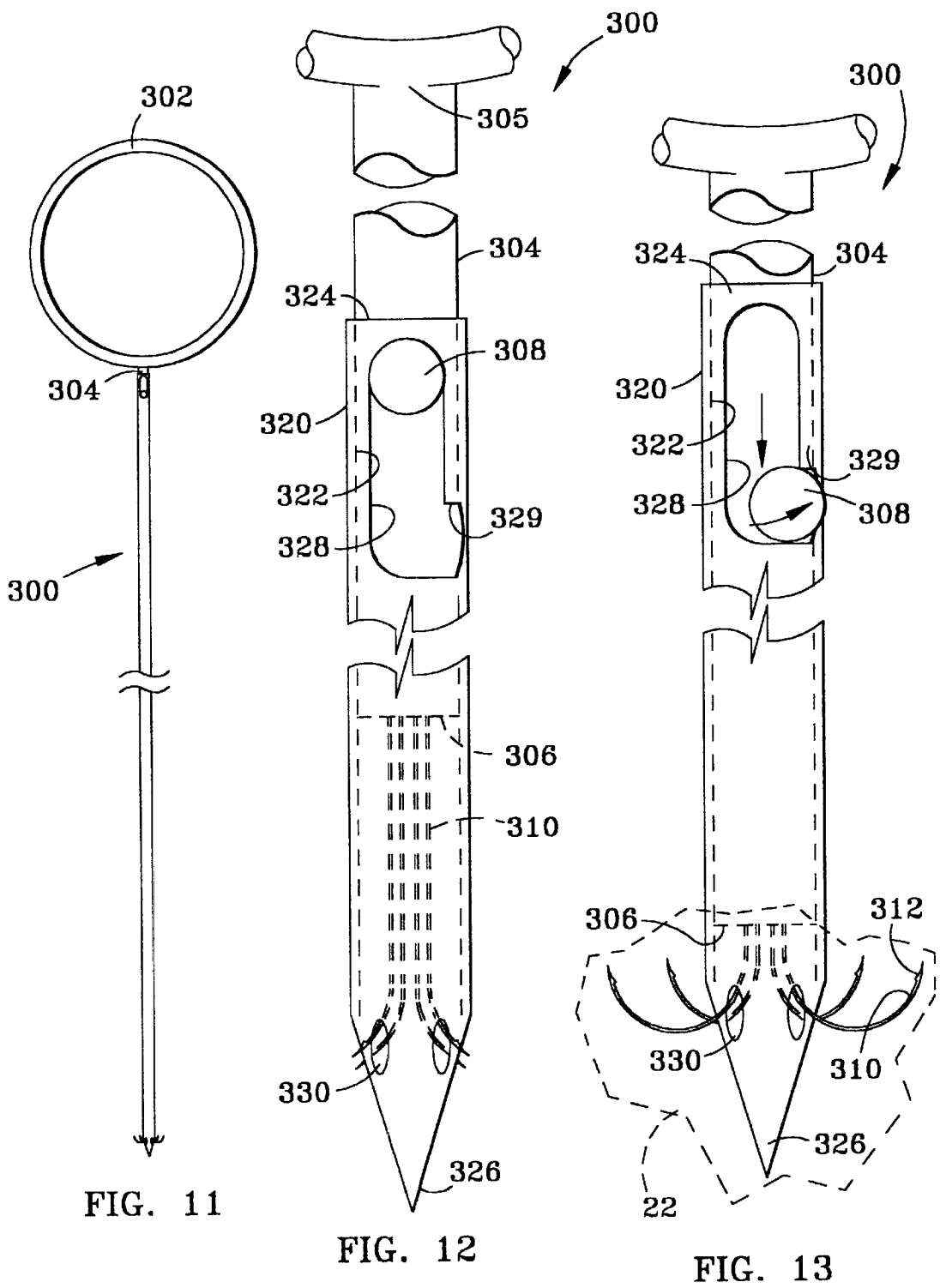
FIG. 11 is a front elevation view of the tissue anchor of the present invention, with the cannula and rod of the cutter being shown in broken view to facilitate illustration.
FIG. 12 is an enlarged view of the tissue anchor in FIG. 11, with the rod and cannula both being broken at first location and the rod alone being broken at a second location to facilitate illustration, also with the rod being shown in a retracted position relative to the cannula.
FIG. 13 is similar to FIG. 12, except that the rod is shown in the extended position relative to the cannula, with the anchor members attached to the end of the rod being shown in an extended position engaged in a portion of a tissue mass.

Turning now to FIGS. 11–13, another aspect of the present invention is tissue anchor 300. The latter is designed to stabilize tissue mass 26 during surgical removal of the mass using system 20, as described in more detail below.

Tissue anchor 300 includes a ring 302 sized to receive the thumb or finger of a user, and a rod 304. The latter includes a proximal end 305, which is attached to ring 302, and a distal end 306. Rod 304 includes an outwardly projecting pin 308 that serves as a stop, as described below. Tissue anchor 300 also includes a plurality of, e.g., four, anchor members 310 that are attached to rod 304 at or adjacent its distal end 306. Typically, anchor members 310 are attached to rod 304 so as to extend away from its distal end 306, as illustrated in FIGS. 12 and 13. However, as an alternative design, anchor member 310 may be attached to rod 304 so as to extend away from distal end 306 toward proximal end 305 (not shown). Each anchor member 310 may terminate with a barb 312 (FIG. 13), if desired. Anchor members 310 preferably have a curved configuration when in an unbiased state, as illustrated in FIGS. 11 and 13. Anchor members 310 are preferably made from spring steel, although other "memory" metal alloys made also be satisfactorily used. In certain applications it may be unnecessary to provide a curve in anchor member 310, i.e., the anchor member may be substantially straight.

Rod 304 preferably, although not necessarily, has a circular cross section. The outside diameter of rod 304 depends upon its intended application, but is typically in the range of 0.3–10 mm, preferably about 1–2 mm. The length of rod 304, as measured between proximal end 305 and distal end 306, also depends upon its desired application, but typically ranges from 5–20 cm.

Tissue anchor 300 also includes a cannula 320 having a central bore 322, a proximal end 324 and a pointed distal end 326. Central bore 322 has an inside diameter that is sized to receive rod 304 with a close sliding fit. Cannula 320 has an outside diameter that is selected based on the intended application but is typically in the range 0.5 mm–12 mm, preferably about 1–3 mm. Cannula 320 also includes an elongate slot 328 that runs parallel to the long axis of the cannula and is sized to receive pin 308 with a close sliding fit. The length of slot 328 is substantially the same as the length of anchor members 310. Slot 328 includes a pocket 329 at its end closest to distal end 326 of cannula 320 that extends orthogonally to the long axis of the slot and is sized to receive pin 308.

Cannula 320 also includes a plurality of apertures 330 extending through the wall of the cannula. Apertures 330 are positioned adjacent distal end 326 of cannula 320 when anchor members 310 are attached to rod 304 to extend away from distal end 306 as illustrated in FIGS. 12 and 13. If anchor members 310 extend from distal end 306 toward proximal end 305 (not shown), then apertures 330 are moved toward the proximal end so that they are spaced from the proximal at least about the length of the anchor members. One aperture 330 is typically provided for each anchor member 310. The lengths of anchor members 310, cannula 320, and slot 328 are together selected so that a small portion, e.g., about 1 mm, of each anchor member 310 projects from its respective aperture 330 when tissue anchor 300 is in the retracted position illustrated in FIG. 12. In this position, pin 308 engages the end of slot 328 closest to proximal end 324. Anchor members 310 are sized in this manner to ensure the anchor members remain positioned in their respective apertures 330 when tissue anchor 300 is in the retracted position illustrated in FIG. 12.

The lengths of anchor members 310, cannula 320, and slot 328 are also together selected so that most, if not substantially the entire, length of the anchor members 310 projects from their respective apertures 330 when tissue anchor is in the extended position illustrated in FIGS. 11 and 13. In this position, pin 308 engages the end of slot 328 closest to distal end 326.

The elements of tissue anchor 300 are preferably made from stainless steel, a plastic such as polystyrene or polyurethane, or other materials suitable for the intended application of the tissue anchor (as described in more detail below) known to those skilled in the art. As noted above, in many cases it is desirable to make anchor members 310 from spring steel or a "memory" metal alloy.

Bracketing

Figure 14:
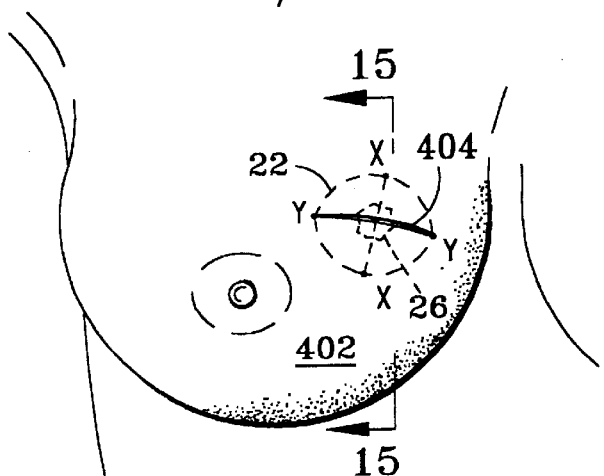
FIG. 14 is a top view of a breast of woman in a supine position, with a tissue mass being surrounded by markers of the present invention so as to define the tissue volume to be removed, and with an incision formed in the skin of the breast above the tissue volume.
Figure 15:
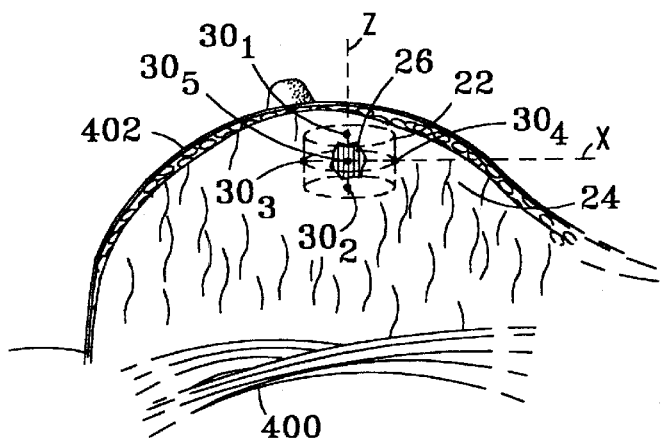
FIG. 15 is a cross-sectional view of the breast of FIG. 14 taken along line 15—15 in FIG. 14.

Referring now to FIGS. 1, 14 and 15, markers 30 may be used to bracket (i.e., define the boundaries of) tissue volume 22 in a tissue portion 24 in accordance with the following method. In the following description of the method of bracketing tissue volume 22, the latter is contained in a human breast. However, it is to be appreciated that tissue volume 22 may be present in other organs and structures, e.g., a liver, or may constitute an entire organ or structure.

As the first step in bracketing tissue volume 22, a tissue mass 26 of interest is identified through conventional imaging methods, e.g., ultrasound, MRI, X-ray or CAT scan. Next, markers 30 are implanted in tissue portion 24 surrounding tissue mass 26 and defining outer boundaries of tissue volume 22. The number of markers 30 used, and the placement of the markers relative to tissue mass 26, will vary depending upon the location of the tissue mass relative to other types of tissue, e.g., bone or muscle, surgeon preference, size and configuration of the tissue mass and the desired amount of tissue margin 28 (FIG. 1) beyond the edge of tissue mass 26. However, in many applications, it is desirable to use at least six markers 30 to bracket tissue volume 22, preferably two on each of axes X, Y and Z (see FIGS. 1, 14 and 15). Preferably the two markers 30 are positioned on each of axes X, Y and Z so as to lie on opposite boundaries of tissue volume 22.

For example, as illustrated in FIG. 1, marker 30, lies on the Z axis at the upper surface of tissue volume 22, marker $30_2$ lies on the Z axis at the lower surface of the tissue volume, marker $30_3$ lies on the X axis at a first location on the outer surface of the tissue volume, marker $30_4$ lies on the X axis at a second location on the outer surface of the tissue volume diametrically opposite marker $3_3$, marker $30_5$ lies on the Y axis at a third location on the outer surface of the tissue volume and marker $30_6$ lies on the Y axis at a fourth location on the outer surface of the tissue volume diametrically opposite marker $30_5$.

While it is preferred that axes X, Y and Z be mutually orthogonal, as illustrated, this is not mandatory and can be difficult to precisely implement in practice. However, it is generally preferable that tissue volume 22 be completely surrounded by markers 30, i.e., that the tissue volume be defined in three dimensions by the markers. One notable exception to this preference is that the marker 30, such as marker $30_2$ shown in FIGS. 1 and 15, positioned at the base of, i.e., underneath, tissue volume 22 is not typically required when a different type of tissue, such as pectoral muscle 400 (FIG. 15) is located at or near where the marker would be positioned. The illustration of marker $30_2$ in FIG. 15 is not inconsistent with this recommended placement regime for markers 30 because of the relatively great spacing between the marker $30_2$ and pectoral muscle 400. Similarly, when the marker 30, such as marker $30_1$ shown in FIG. 1, to be positioned on top of tissue volume 22 is near the skin overlying the tissue volume, such marker is not typically required. Also, while the X, Y and Z axes are illustrated in FIG. 1 as intersecting at a common point centrally located within tissue mass 26, this is not required. For example, it may be desirable to offset the X and Y axes somewhat, as measured along the Z axis. Furthermore, in some cases it may be desirable to define tissue volume 22 with markers 30 in only two dimensions or in only one dimension.

Figure 1A:
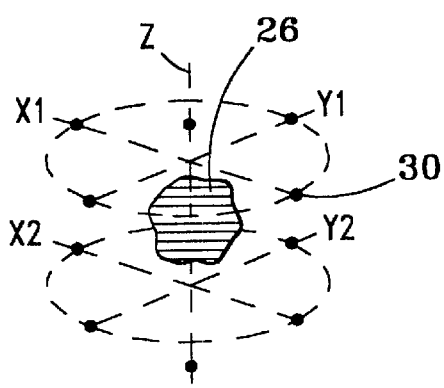
FIG. 1a is a perspective view of the tissue mass illustrated in FIG. 1, with two markers being positioned on opposite ends of each of mutually orthogonal X1, Y1 and Z axes and with two markers being positioned on opposite ends of mutually orthogonal X2 and Y2 axes which are mutually orthogonal with respect to the Z axis and offset along with Z axis with respect to the X1 and Y1 axes.
Figure 1B:
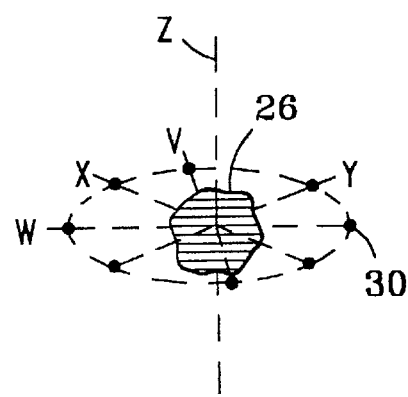
FIG. 1b is a perspective view of the tissue volume illustrated in FIG. 1, with two markers being positioned on opposite ends of each of V, W, X and Y axes, all of which lie in a common plane and are mutually orthogonal with respect to a Z axis, all of these axes intersecting the tissue mass.

In some cases, it will be desirable to use more than two markers 30 on X, Y and Z axes. Referring to FIG. 1a, in a first case, ten markers 30 are used, two on the Z axis, two on an axis $X_1$, two on an axis $X_2$ that is offset along the Z axis with respect to axis $X_1$, two on an axis $Y_1$, and two on an axis $Y_2$ that is offset along the Z axis with respect to axis $Y_1$. Referring to FIG. 1b, in a second case, ten markers 30 are used, two on the X axis, two on the Y axis, two on the Z axis, two on the V axis which bisects the X and Y axes and two on the W axis which also bisects the X and Y axes, but at a different location. Other numbers and relative placements of markers are also encompassed by the present invention.

Markers 30 are preferably spaced from tissue mass 26 so as to define tissue volume 22 such that tissue margin 28 is large enough to ensure none of the tissue mass lies outside the tissue volume. This precise spacing will vary with the nature of the tissue mass 26, the size of the tissue mass, surgeon preference and other factors. However, tissue margin 28, as measured outwardly along an axis extending perpendicular to a surface location on tissue mass 26, is generally about 0.5 cm to 3 cm, and is preferably about 1 cm to 2 cm.

Markers 30 may be implanted in tissue portion 24 in a variety of different ways using a variety of different tools. In general, markers 30 are implanted using a conventional imaging system (not shown) that simultaneously generates an image of tissue mass 26 and the markers. By frequently comparing the location of markers 30 to tissue mass 26 during implantation of the markers into tissue portion 24, based on image information received from the imaging system, the markers may be positioned so as to define tissue volume 22 in the manner described above. As noted above, markers 30 are made from a material that provides good image contrast with respect to the imaging energy used.

It is preferable to at least partially immobilize tissue portion 24 during implantation of markers 30. However, this is less critical than might be expected because by comparing the relative location of a marker 30 to tissue mass 26, the desired relative placement can typically be achieved, even if tissue portion 24 is moving during marker implantation.

Marker Implantation

Various techniques may be used to implant markers 30 in tissue portion 24. With reference to FIGS. 14 and 15, one approach is to insert markers 30 percutaneously through skin 402 overlying tissue portion 24 using known needle pushers or implanters (neither shown) of the type used to implant "seeds" of radioactive material for various cancer treatments. For example, needle pushers of the type sold by Best Industries of Springfield, Virginia, may be satisfactorily employed. These needle pushers include a central needle surrounded by an outer tube having an end plate or cup for supporting the radioactive "seed." Following insertion of the needle pusher into the selected tissue mass, the radioactive "seed" is released by pressing the central needle downwardly relative to the surrounding outer tube, with the point of the needle ejecting the "seed" from the end plate or cup of the outer tube.

To percutaneously insert marker 30 in accordance with this first approach, the marker is positioned on the end of the needle pusher (in place of the radioactive "seed"), is forced through skin 402 and, using feedback from the imaging system, is guided to the region where it is desired to implant the marker. Then the marker 30 is ejected from the needle pusher by urging the central needle forwardly into the inner tube.

A second approach for implanting markers 30 involves creating a small, e.g., 5–10 mm, incision (not shown) in the skin 402 (see FIGS. 1 and 14) overlying tissue portion 24. Next, a scalpel is inserted through the incision so as to form a slit in the underlying tissue portion extending to the position where it is desired to implant a maker 30. Then a marker 30 is inserted through the slit to such position using a tweezers, needle pusher, trocar or other suitable tool. Other markers 30 are implanted through separate incisions in skin 402 in similar manner so as to bracket tissue volume 22.

Figure 16:
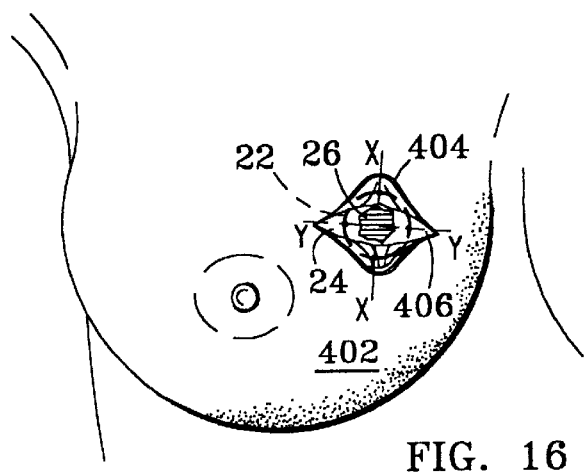
FIG. 16 is similar to FIG. 14, except that the skin adjacent the incision has been pulled apart to provide access to underlying breast tissue.

Referring now to FIGS. 1 and 14–16, a third approach for implanting markers 30 is to form a relative large, e.g., 1–3 cm, incision 404 (see FIG. 14) in skin 402 overlying tissue mass 26. Next, incision 404 is pulled open as illustrated in FIG. 16 using retractors or other conventional devices so as to form a relatively large open region 406 above tissue mass 26. Markers 30 are then implanted into tissue portion 24 using either the first or second approaches described above.

Other approaches for implanting markers 30 so as to bracket tissue mass 26 are also encompassed by the present invention. The speed and accuracy with which markers 30 may be implanted, and minimizing trauma associated with implantation, are important objectives to consider in selecting other approaches for implanting markers 30.

Marker Identification

Once tissue mass 26 has been bracketed in the manner described above, tissue volume 22 can be removed using either of two procedures encompassed by the present invention. As described in more detail below, the first procedure involves identifying the boundaries of tissue volume 22 using an embodiment of probe 32 and detector 34 that is appropriate for the type of marker 30 used, as discussed above. Using information from detector 34 regarding such boundaries, tissue volume 22 is then removed using a scalpel, cutter 200 or other tool, with tissue anchor 300 preferably, but not necessarily, being used to stabilize the tissue volume during removal.

The second procedure is similar to the first, except that tissue anchor 300 is not used.

For both the first and second procedures for removing tissue volume 22, as the first step the surgeon typically identifies the boundaries of the tissue volume using system 20. This step is generally needed because in practice markers 30 will often be implanted by another doctor, e.g., a radiologist, as a separate procedure. The boundaries of tissue volume 22 are identified by moving probe 32 in the general region of the tissue volume and then monitoring the detection information (e.g., sound, light, dial movement, image clarity and the like) provided by detector 34. As noted above, detector 34 may provide this information when probe 32 is moved within a predetermined proximity of a given marker 30, or may provide this information in a form that changes with changes in proximity of the probe to the marker (e.g., a light gets brighter as the probe is moved toward a marker and dimmer as it is moved away).

The interaction between marker 30 and probe 32 and detector 34 depends upon the detection characteristic of the marker. In the case of marker 30a, which emits gamma rays 40 (FIG. 2a) on a continuous basis, a probe and detector of the type described in U.S. Pat. Nos. 5,170,055 and 5,246,005 to Carroll et al. (the "C-TRAK probe"), as discussed above, may be satisfactorily used to detect the markers. The C-TRAK probe includes a radiation detector, e.g., a scintillation crystal, which provides an output signal that is believed to vary as a function of the flux density of the gamma rays 40 emitted by marker 30a. Changes in this output signal are then converted into humanly recognizable detection information, e.g., sound, having a characteristic, i.e., pitch or tempo in the case of sound, that varies with changes in gamma ray flux density. By observing the location of probe 32 when the detection information from detector 34 indicates the probe is closest to a given marker 30a, the surgeon can mentally note where the marker is located. Repetition of this process will result in identification of the location of all markers 30a.

Referring to FIGS. 2b and 7, In the case of marker 30b, which generates a magnetic field 42, probe 32' and detector 34' are used to detect the marker. To locate a marker 30b, the surgeon moves probe 32' in the general region of tissue volume 22, with the result that as the probe approaches a given marker 30b its Hall effect sensor (not shown) generates an output signal having a voltage that increases as the probe is moved toward the marker. Similarly the voltage of the output signal decreases as probe 32' is moved away from the marker 30b. The output signal of probe 32' is-provide via line 120 to amplifier 122, which amplifies the output signal from the probe. As discussed above, the amplified-voltage signal from probe 32' is displayed on signal meter 126 and is also delivered to voltage controlled oscillator 128. The latter generates an oscillating signal, the frequency of which varies as a function of the voltage of the amplified signal provided to voltage controlled oscillator 128. This signal is then amplified by amplifier 130, and the amplified signal then drives speaker 116 such that the pitch of the sound provided by the speaker 116 varies as a function of proximity of probe 32' to marker 30b. By observing signal meter 126 and/or listening to speaker 116, the surgeon can assess when the probe 32' is positioned closest to a selected marker 30b. Repetition of this process will result in identification of the location of all of markers 30b.

Turning now to FIGS. 2c, 3a, 3b and 8, marker 30c, which generates an RF signal 44, is identified using probe 32" and detector 34" in the following manner. RF exciter 60 is operated so as to produce an RF exciter signal 46. More particularly, radio frequency generator 62 (FIG. 3b) generates a radio frequency signal which is amplified by RF amplifier 64, following sensitivity adjustment using gain adjustment 66, with the amplified signal being provided to antenna 68 for transmission to markers 30c. RF exciter 60 is positioned sufficiently close to markers 30c that RF exciter signal 46 is received by antenna 52 of the markers and is of sufficient strength to drive radio frequency generator 56 of the markers. Following detection and regulation by circuit 54 (FIG. 3a) of the signal 46 received by antenna 52, radio frequency generator 56 generates an RF signal which is transmitted by antenna 52 as RF signal 44. Preferably, but not necessarily, each marker 30c transmits RF signal 44 at a frequency that is unique to the marker, while an RF exciter signal 46 having a single frequency is preferably used for all of the markers 30c, with the frequency of signal 46 being different than the frequency of signal 44.

Once exciter 60 has been activated so as to cause marker 30c to generate RF signal 44, detection of the marker commences. This is achieved by positioning probe 32" (FIG. 8) on or adjacent skin 402 adjacent tissue volume 22, and then monitoring proximity information provided by analog signal strength display 150 and/or speaker 116 of detector 34". More specifically, following receipt of RF signal 44 by receive antenna 140 of probe 32", the signal is filtered by selectable notch filter 142 of probe 32". By correlating a given marker 30c, e.g., marker $30c_1$, with a corresponding representation on the adjustment knob (not shown) that controls selectable notch filter 142, e.g., the reference number "1," the surgeon can identify the location of the given marker. The knob for adjusting selectable notch filter 142 is then moved to a different position when detecting a second marker 30c, e.g., marker $30c_2$.

Signals from receive antenna 140 that are passed through selectable notch filter 142 are then amplified by RF amplifier 144 with the adjustment of the amplifier gain being provided as needed using gain adjustment 146. The amplified signal is then provided to rectifier/integrator 148 where the signal is rectified and time filtered. The strength of signal 144 detected by detector 34" is then displayed via analog signal strength display 150 and is provided to voltage controlled oscillator 152. The latter creates an oscillating signal, the frequency of which varies as a function of the voltage of the signal provided by rectifier/integrator 148. The output signal from voltage controlled oscillator 152 is then amplified by audio amplifier 154 and delivered to drive speaker 116. The pitch of the sound provided by speaker 116 will vary as a function of the frequency of the signal provided by voltage controlled oscillator 152, and as an ultimate function of the proximity of probe 32" to a given marker 30c. By observing the location of probe 32" when the detection information from detector 34" indicates the probe is closest to a given marker 30c, the surgeon can mentally note where the marker is located. By repeating this process for each of the markers 30c with appropriate adjustment of selectable notch filter 142, all of the markers 30c may be located.

Referring to FIGS. 2d, 3a, 3b and 8, marker 30d may also be detected using detector 34" in substantially the same manner discussed above with respect to marker 30c. One significant difference, however, is the fact that RF exciter 60 (FIG. 3b) is not used insofar as marker 30d contains its own power source.

Turning next to FIGS. 2e, 2f, and 4–6, for makers 30e and 30f, which are designed to provide high image contrast when imaged with ultrasound, probe 32 includes a conventional ultrasound transducer (not shown) that generates ultrasound in a conventional frequency range, e.g., 7.5 MHz, and receives back reflection of the ultrasound signal. Detector 34 is the image processor and display (neither shown) of a conventional ultrasound apparatus which is connected to the ultrasound transducer. Markers 30e or 30f are identified by scanning the general region of tissue volume 22 with probe 32, and monitoring the ultrasound image of the markers provided by detector 34. This ultrasound image permits the surgeon to identify the placement of all of the markers, and hence the boundaries of tissue volume 22.

In the case of marker 30e, the latter is caused to vibrate at a frequency that is generally significantly less than that of the ultrasound generated by the ultrasound transducer in probe 32. This creates, through what is believed to be a Doppler shift phenomenon, enhanced image contrast in the ultrasound signal reflected off markers 30e. Vibration of a marker 30e is effected by operating RF exciter 92 so that radio frequency generator 94 generates a radio frequency signal which is amplified by amp 96 and then transmitted by antenna 100. Antenna 80 of marker 30e receives this RF signal, which is detected and regulated by circuit 84 so as to generate an oscillating electrical signal that is provided to piezo-electric device 86. This signal causes the piezo-electric device 86 to mechanically oscillate, which oscillations are transferred via support 88 to outer housing 90 of marker 30e, thereby causing the housing (and hence the marker) to vibrate.

Tissue Removal

Following identification of tissue volume 22 using the procedures outlined above, surgical removal of the tissue volume commences. Referring to FIGS. 14 and 16, the first of the two procedures for removing tissue volume 22 referenced above commences with the formation of an incision 404 (FIG. 14) in skin 402 above tissue volume 22. The length of incision 404 is typically about equal to, or slightly greater than, the distance between two markers 30 lying on a given axis, e.g., the Y axis as illustrated in FIG. 14. Next, portions of skin 402 adjacent incision 404 are pulled apart by retractors or other known devices, so as to form open region 406 (FIG. 16) and expose tissue portion 24 beneath.

Figure 17:
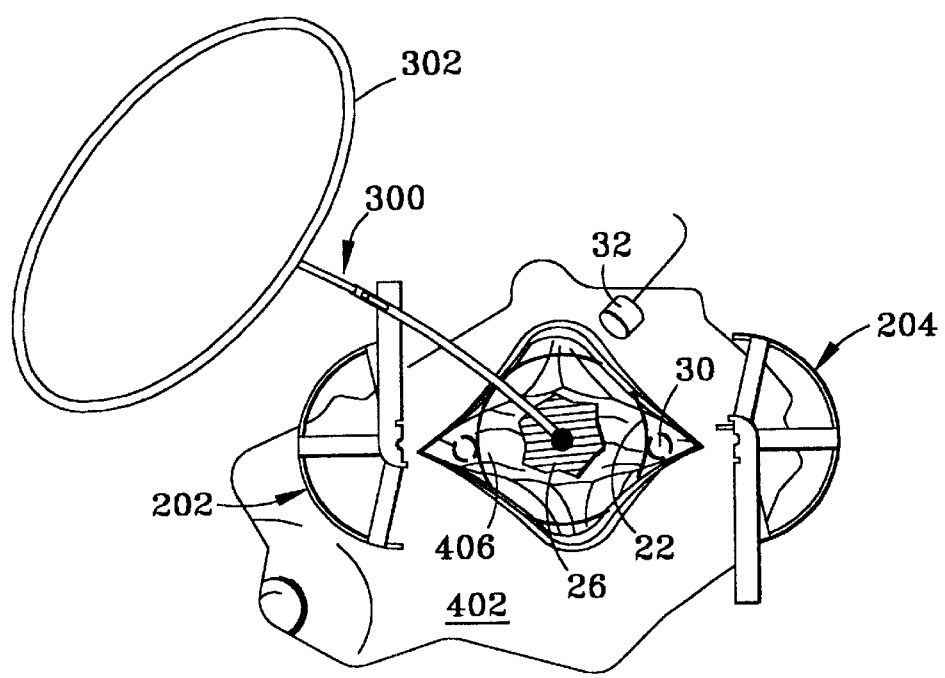
FIG. 17 is an enlarged view of the incision of FIG. 16, with the tissue anchor illustrated in FIGS. 11–13 being positioned in the tissue mass, and the two portions of the cutter illustrated in FIGS. 9 and 10 and probe of the present invention all being positioned adjacent the surgical cavity.
Figure 18:
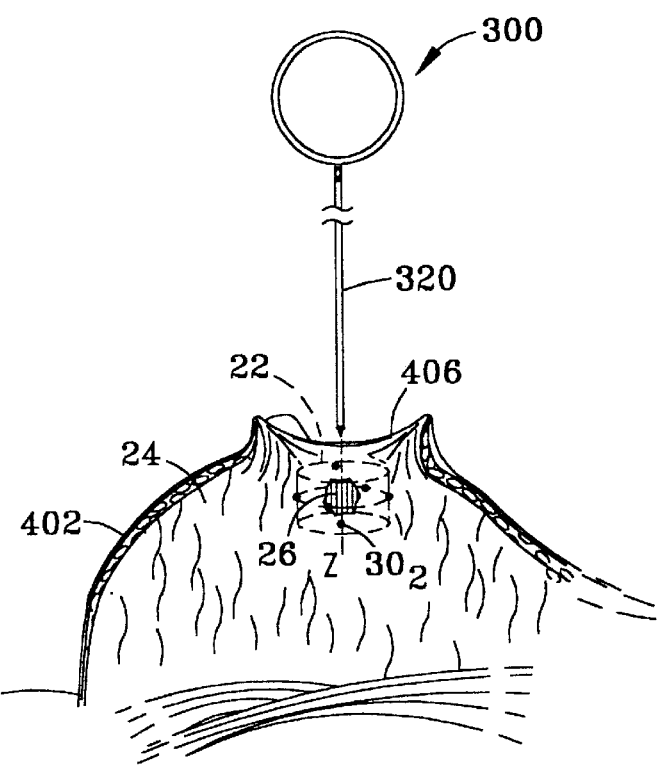
FIG. 18 is similar to FIG. 15, except that an incision has been formed in the skin of the breast and has been retracted to provide access to the underlying tissue mass to be removed and the tissue anchor has been positioned above the breast.
Figure 19:
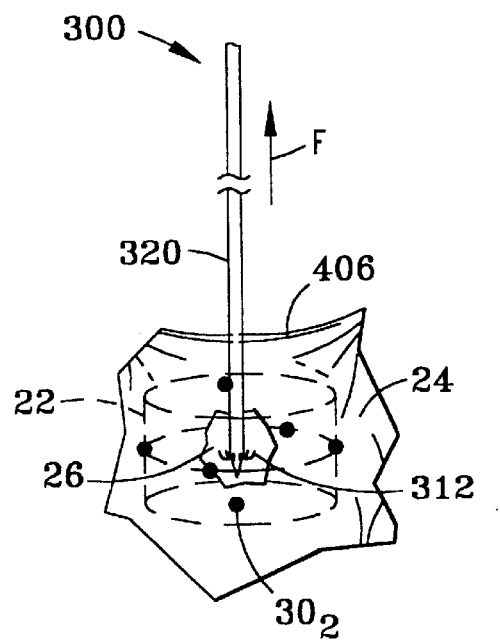
FIG. 19 is an enlarged view of the portion of the breast illustrated in FIG. 18 containing the tissue mass to be removed, with the tissue anchor being positioned in the tissue mass in the extended position so that the anchor members of the tissue anchor engage the tissue mass.

Referring now to FIGS. 11–13 and 17–19, as the next step, tissue anchor 300 is inserted in tissue mass 26 so as to assume the extended position illustrated in FIG. 13. This is achieved by inserting a finger into ring 302, then pulling rod $30_4$ upwardly (as illustrated in FIG. 12) with respect to cannula 320 so that pin 308 moves in slot 328 toward the end thereof closest to proximal end 324 of the cannula. In this retracted position, cannula 320 is grasped and is inserted through open region 406 into tissue volume 22 so that its distal end 326 is positioned substantially in the center of tissue mass 26. This placement may be achieved under the guidance of an imaging system (not shown) that is capable of imaging tissue anchor 300, e.g., ultrasound or X-ray imaging systems. Alternatively, using system 20, the location a marker $30_2$ lying beneath tissue volume 22, as illustrated in FIGS. 18 and 19, is identified using the procedure described above to identify the tissue volume. By identifying the depth at which marker $30_2$ is located and comparing this to the length of cannula 320 inserted into tissue volume 22, distal end 326 may be positioned centrally within tissue mass 26.

Next, ring 302, and hence rod 304 attached thereto, is forced downwardly (as viewed in FIG. 17) relative to cannula 320 until pin 308 contacts the end of slot 328 closest to distal end 326. As rod 304 moves within cannula 320 toward this extended position, anchor members 310 are forced out through apertures 330 and into tissue mass 26 (see FIG. 19). Then, ring 302, and hence rod 304, is rotated slightly so as to cause pin 308 to move into pocket 329.

Figure 20:
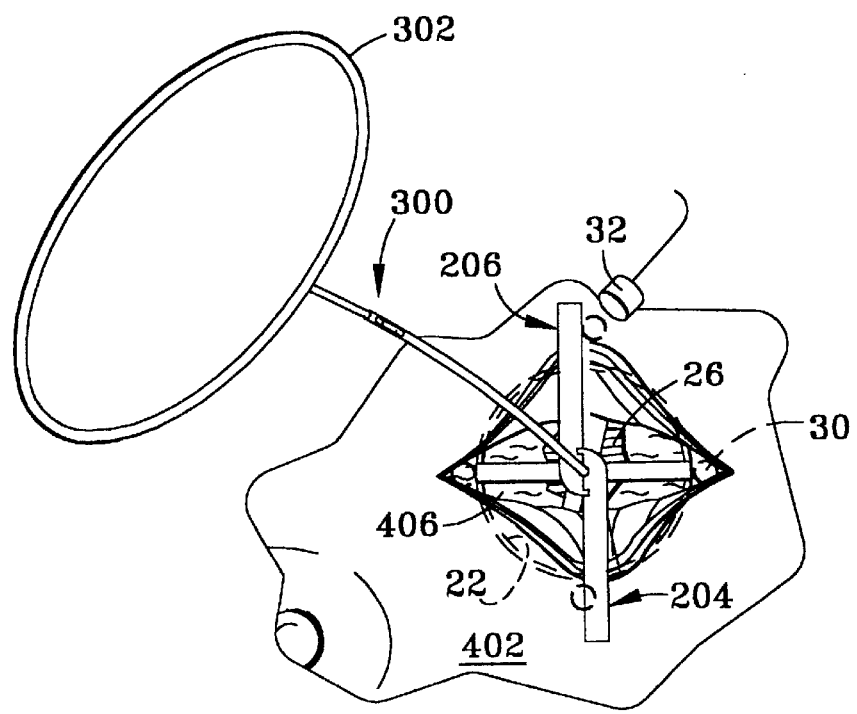
FIG. 20 is similar to FIG. 17, except that the two portions of the cutter are illustrated in engaged, cooperative relationship and are positioned under the skin in contact with the tissue volume to be removed.

The next step in the removal of tissue volume 22 is assembly and placement of cutter 200 in open region 406. Referring to FIGS. 9, 10, 17 and 20, cutter portions 202 and 204 are positioned adjacent open region 406, as illustrated in FIG. 17. Next, cutter portion 202 is positioned in open region 406, with its curved plate 206 being inserted under portions of skin 402 adjacent the open region, as illustrated in FIG. 20. Next, cutter portion 204 is similarly positioned in open region 406. Then, portions 202 and 204 are moved toward one another so that cannula 320 of tissue anchor 300 is received in elongate groove 232 in central handle section 222 and in elongate groove 255 in central handle section 252. Portions 202 and 204 are moved even closer to one another so that central handle sections 222 and 252 engage one another and so that projections 258 and 260 are received, respectively, in apertures 228 and 230. When positioned in this manner, ends 208 and 210 of curved portion 206 of cutter portion 202, engage, respectively, ends 240 and 238 of curved portion 236 of cutter portion 204, so as to form a substantially continuous curved cutting edge consisting of cutting edges 212 and 242. Also when positioned in this manner, longitudinal axis 262 of cutter 200 extends substantially parallel to the elongate axis of cannula 320, both of which are substantially co-axial with the Z axis extending through tissue volume 22. (See FIGS. 18 and 21).

Figure 21:
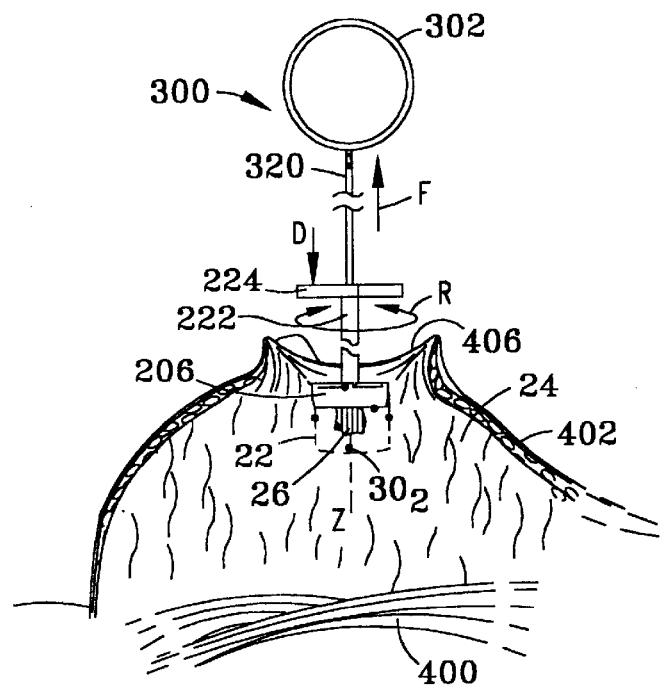
FIG. 21 is similar to FIG. 18, except that the tissue cutter is illustrated surrounding the tissue anchor and in cutting engagement with the tissue volume to be removed.

Next, the position of cutter 200 relative to markers 30 is determined by comparing the location of markers, which is typically determined by using probe 32 and detector 34 in the manner described above, to the position of the cutter. Then, the location of cutter 200 is adjusted so that axis 262 of cutter 200 is substantially co-axial with Z axis tissue volume 22, as illustrated in FIG. 21. In some cases the surgeon will recall the location of markers 30 from the prior marker identification step, and so it will be unnecessary to again locate the markers. However, when tissue portion 24 is amorphous and pliable, as is the case when breast tissue is involved, it is recommended that this alignment of cutter 200 with tissue portions 30 using probe 32 and detector 34 be performed before any cutting of tissue volume 22 commences.

In connection with the initial insertion of cutter 200 in open portion 406, an appropriately sized cutter 200 is selected such that the radius of curved plates 206 and 236, as measured radially outwardly from axis 262, is substantially the same as the radius of tissue volume 22 as measured radially outward from the Z axis. While this relationship between the radii of curved plates 206 and 236 of cutter 200 and the radius of tissue volume 22 as measured with respect to Z axis, is preferred, in some cases it may be satisfactory to use a cutter having a radius that is greater than or less than the radius of the tissue volume 22. Also, the height of curved portions 206 and 236 is another factor considered in selecting an appropriate cutter 200.

Referring to FIGS. 18–22, as the next step in the removal of tissue volume 22, ring 302 of tissue anchor 300 is typically pulled upwardly in the direction of arrow F (see FIGS. 19 and 21) sufficiently to tension tissue volume 22 and adjacent portions of tissue portion 24. By this tensioning of tissue volume 22 and tissue portion 24 the tendency of the tissue portion to compress under the force of a cutting device is reduced. Also, this tensioning of tissue volume 22 serves to stabilize the tissue volume during the surgical removal process.

In some cases, sufficient tissue stabilization can be achieved merely by holding tissue anchor 300 in a substantially fixed position relative to tissue volume 22. In other words, no force in the direction of arrow F is applied to tissue anchor 300 except as may be necessary to hold the tissue anchor in a stable position.

Then, while stabilizing tissue volume 22 with tissue anchor 300, preferably, but not necessarily by maintaining an upward force on the tissue anchor, the surgeon grips handles 220 and 250 of cutter 200 and begins pressing downwardly on the handles toward tissue volume 22, i.e., in the direction of arrow D (see FIG. 21). At the same time, handles 220 and 250 are rotated about cutter axis 262 in either or both a clockwise and counterclockwise direction, i.e., in the direction indicated by curved arrow R (see FIG. 21). Elongate grooves 232 and 255 are sized to permit cutter 200 to rotate relatively freely about cannula 320 positioned therein. Pins 258 and 260 and associated apertures 228 and 230 are provided to ensure portions 202 and 204 remain operatively engaged with one another as illustrated in FIG. 10, and so that the portions rotate together when a rotational force is applied to one of the portions.

As cutter 200 is rotated about its axis 262 and is urged downwardly towards tissue volume 22, bottom edges 212 and 242 begin cutting tissue volume 22 along its outer boundary. Progress in removing tissue volume 22 is generally periodically determined by comparing the position of curve plates 206 and 236 of cutter 200 relative to markers 30 using probe 32 and detector 34 to identify the locations of markers 30 and then comparing such locations with the location of the cutter. In particular, a determination can be made as to when tissue volume 22 has been severed from tissue portion 24 to a depth defined by marker $30_2$ (FIG. 21) defining the bottom or innermost portion of the tissue volume. Thus, by iteratively comparing the position of cutter 200 to the locations of markers 30 using marker location information acquired from detector 34 based on proximity information provided by the detector, a surgeon can determine when the cutting operation is completed and cutter 200 can be removed from tissue portion 24, as indicated in FIG. 22.

Figure 22:
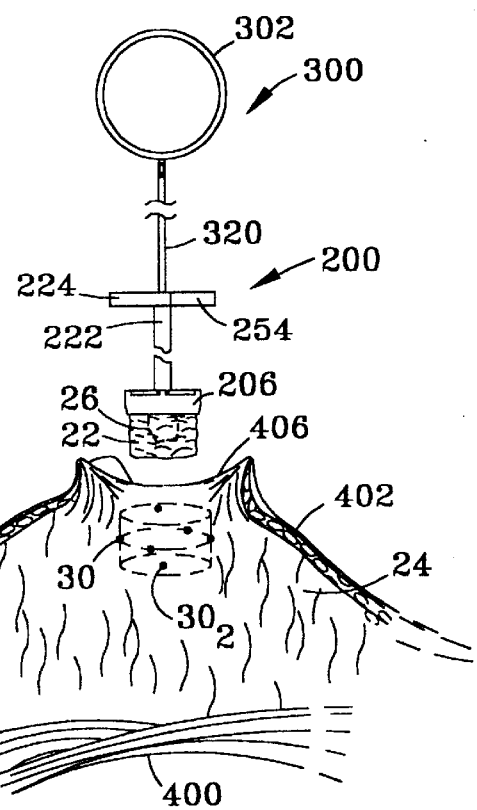
FIG. 22 is similar to FIG. 21, except that the tissue volume has been completely removed from the breast and is illustrated immediately above the surgical opening in engagement with the tissue anchor and cutter.

Depending upon the size of cutter 200 relative to the placement of markers 30, the latter may remain in place in tissue portion 24 following removal of tissue volume 22, as indicated in FIG. 22. If such as the case, markers 30 are then subsequently removed by first locating the markers using probe 32 and detector 34 and then removing the markers with a suitable instrument, e.g., tweezers. In other cases, the markers will be included in the tissue volume 22.

In some cases, it will be necessary to sever the bottom or innermost portion of tissue volume 22 from tissue portion 24 so as to permit removal of the tissue volume. A scalpel or other conventional tool may be used to perform this final severing of the tissue volume. The precise location where this final incision is made may be determined by again locating the position of marker $30_2$ using probe 32 and detector 34. By leaning tissue anchor 300 and cutter 200 to one side, a surgeon can typically follow the incision created by cutter 200 with a scalpel or other tool down to the region where marker $30_2$ is located and tissue volume 22 remains attached to tissue portion 24.

As noted above, in some circumstances a marker $30_2$ is not required when the bottom or innermost portion of tissue volume 22 is positioned immediately above a different type of tissue, e.g., a pectoral muscle 400. In such case, the surgeon can assess when cutter 200 has been inserted sufficiently deep into tissue portion 24 by merely observing when bottom cutting edges 212 and 242 are about to engage the different type of tissue.

Referring to FIG. 1a, by inserting markers 30 at staggered locations along the Z axis, the relative depth of cutter 200 in tissue portion 24 can be determined by locating specific markers using probe 32 and detector 34. The location of such markers 30 is then compared with the location of cutter 200 to determine the depth of the cut. For example, if markers 30c are installed at positions $X_1$ and $X_2$ in FIG. 1a, and each marker has a unique frequency, these markers can be uniquely identified by detector 34" (FIG. 8) in the manner described above.

Referring to FIG. 1b, by positioning more than four markers, e.g., eight markers as illustrated in FIG. 1b, the boundaries of tissue volume 22 can often be more readily defined during the removal of the tissue volume. This is so because increasing the number of markers 30 used increases the quantity of information received from detector 34 regarding the boundaries of tissue volume 22.

While the use of cutter 200 in connection with the removal tissue volume 22 often expedites removal of the tissue volume, use of the cutter is not a mandatory aspect of the present method of bracketing and removing the tissue volume. In this regard, a conventional scalpel may often be satisfactorily employed in place of cutter 200. Also, under certain circumstances it may be desirable to initiate an incision with cutter 200, and then complete the incision with a scalpel.

The process of removing tissue volume 22 using a scalpel also preferably commences by inserting tissue anchor 300 in tissue volume 22 in the manner described above. The location of markers 30 are also determined prior to and during the removal of tissue volume 22 by scalpel in the manner described above. Thus, during the removal of tissue volume 22, the boundaries thereof may be repeatedly identified by locating markers 30 using probe 32 and detector 34. As noted above, it is generally advantageous to use tissue anchor 300 when removing tissue volume 22 with a scalpel because by stabilizing the tissue volume and surrounding regions of tissue portion 24, it is easier to maintain alignment of the scalpel with the boundaries of the tissue volume. However, it is to be appreciated that the use of tissue anchor 300 is a preferred, but not essential, aspect of the present method of bracketing and removing tissue volume 22.

Referring now to FIG. 2g and FIG. 15, as noted above, probe 32 and detector 34 are not used in connection with marker 30g. The detection characteristic of markers 30g is the release of a colored dye 78 in surgical cavity adjacent the markers. Removal of a tissue volume 22 bracketed by markers 30g differs from the removal of tissue volume when bracketed by the other embodiments of marker 30 in that the location of marker 30g is not determined by the surgeon prior to initiation of the removal of tissue volume 22. Practically speaking, this is more a difference in the process for removing tissue volume 22 than a difference in the composition and construction of marker 30g. This is so because for implantation purposes, marker 30g must necessarily be imagable by some form of imaging system, which imaging system could, in most cases, also be used by the surgeon to identify the location of marker 30g prior to and in connection with the removal of tissue volume 22. For example, if marker 30g is initially implanted by imaging the marker using an ultrasound system, then marker 30g is actually a marker 30f. Thus, in connection with the following description of the process of removing tissue volume 22 bracketed with markers 30g, it is assumed the markers are not located by the surgeon prior to, or in connection with, the removal of tissue volume other than by visual observation, as discussed below.

Removal of tissue volume 22 bracketed by markers 30g also preferably commences by installing tissue anchor 300 as described above. Again, the use of tissue anchor 300 is preferred, but not mandatory. Next, the surgeon commences cutting the general region of tissue volume 22, which can be defined by colored marks, Kopanz needles or other known techniques. Then, the removal of tissue volume 22 proceeds using either cutter 200, or a scalpel or other cutting device, as described above. As this removal of tissue volume 22 is performed, tissue anchor 300, if used, is manipulated to stabilize tissue volume 22 in the manner described above. As cutter 200, the scalpel or other cutting device encounters a marker 30g, the capsule of the marker is severed releasing the colored dye 78. This advises the surgeon that a boundary of tissue volume 22 has been encountered. It may be advantageous to use a given color of dye in markers 30g defining one side of the boundary of tissue volume 22, while the markers 30g defining an opposite side include a different color of dye. By defining the boundary of tissue volume 22 with a sufficient number, e.g., 10–25, of markers 30g, the boundary of tissue volume 22 can typically be identified by iteratively cutting and observing whether dye appears in the surgical cavity.

As noted above, marker embodiments 30a–30f may all include colored dye 78 within an outer capsule that is sufficiently tough to withstand insertion and yet is relatively easily cut by cutter 200, a scalpel or other cutting device. Such use of dye in markers 30 provides another source of information for the surgeon regarding the boundary of tissue volume 22.

An important advantage of tissue bracketing system 20 is that is permits the relatively precise identification of the boundaries of tissue volume 22 without the need for needles, wires or other cumbersome apparatus projecting from tissue portion 24. As such, bracketing system permits a surgeon to relatively quickly and easily identify the tissue boundary of tissue volume 22 and remove the tissue volume. In addition, system 20 is ideally adopted for bracketing a tissue volume 22 in amorphous, pliable tissue, such as breast tissue.

An important advantage of cutter 200 is that it permits a tissue volume 22 of relatively large diameter to be removed through a relatively small incision 404. This advantage is important in this era when tissue-conserving therapies are being emphasized.

By stabilizing tissue volume 22 using tissue anchor 300, the accuracy with which a surgeon can remove tissue volume 22 is enhanced. This advantage of the present invention arises because tensioning of the tissue volume 22 by pulling upwardly on tissue anchor 300 serves to retain the tissue portion in a relatively stable position. Indeed, even holding tissue anchor 300 in a substantially fixed position relative to the tissue volume 22 with which it is engaged typically provides beneficial stabilization of the tissue volume.

While cutter 200 and tissue anchor 300 may be advantageously employed in connection with the present method of bracketing and removing tissue volume 22, it is to be appreciated that the cutter and tissue anchor have application in many other contexts. More specifically, in any application in which it is desired to remove a volume of tissue through as small an incision as possible, cutter 200 has important utility. Similarly, when it is desired to stabilize a piece of tissue in connection with surgical removal or other treatment of the piece of tissue, whether or not within the bracketing context of the present invention, tissue anchor 300 also has important application.

Since certain changes may be made in the above apparatus and processes without departing from the scope of the present invention, it is intended that all matter contained in the preceding description or shown in the accompanying drawings shall be interpreted in an illustrative and not in a limiting sense.

What is claimed is:

1. A system for defining a boundary of a tissue volume, comprising:
   a. a plurality of markers having a maximum dimension of no more than 5 mm, as measured along any axis extending through each of the plurality of markers, wherein each of the plurality of markers includes:
      A. an antenna;
      B. a circuit connected to the antenna for generating a radio frequency signal, in response to receipt of an exciter signal, having a frequency that is different from frequencies of the radio frequency signals generated by other markers of the plurality of markers; and
      C. an exciter for generating the exciter signal, wherein the exciter signal does not include a radio frequency signal having a frequency that is the same as frequencies of the radio frequency signals generated by the plurality of markers;
   b. a probe; and
   c. a detector connected to the probe that provides information when the probe is moved proximate to the plurality of markers.

2. A system for defining a boundary of a tissue volume, comprising:
   a. at least one marker having a maximum dimension of no more than 5 mm, as measured along any axis extending through the at least one marker, wherein the at least one marker vibrates;
   b. a probe; and
   c. a detector connected to the probe that provides information when the probe is moved proximate to the at least one marker.

3. A system for defining a boundary of a tissue volume, comprising:
   a. at least one marker having a maximum dimension of no more than 5 mm, as measured along any axis extending through the at least one marker, wherein the at least one marker includes:
      A. a piezo-electric device that oscillates mechanically in response to an oscillating electrical signal; and
      B. a circuit connected to the piezo-electric device that generates the oscillating electrical signal;

b. a probe; and c. a detector connected to the probe that provides information when the probe is moved proximate to the at least one marker.

4. A system according to claim 3, wherein the at least one marker has a housing that is designed to resonate at a first frequency and the piezo-electric device is coupled to the housing so that mechanical oscillations of the piezo-electric device are transmitted from the piezo-electric device to the housing.

5. A system according to claim 3, wherein the at least one marker includes:

a. an antenna for receiving an exciter signal;

b. wherein the circuit is connected to the antenna and is designed to generate the oscillating electrical signal when the antenna receives the exciter signal; and c. an exciter for generating the exciter signal.

6. A system for defining a boundary of a tissue volume, comprising:

a. at least one marker having a maximum dimension of no more than 5 mm, as measured along any axis extending through the at least one marker, wherein the at least one marker includes a plurality of plates that are configured, positioned and made from a material such that the at least one marker strongly reflects ultrasound energy incident thereon;

b. a probe; and c. a detector connected to the probe that provides information when the probe is moved proximate to the at least one marker.

7. A system for defining a boundary of a tissue volume, comprising:

a. at least one marker having a maximum dimension of no more than 5 mm, as measured along any axis extending through the at least one marker, wherein the at least one marker includes a capsule filled with a colored dye;

b. a probe; and c. a detector connected to the probe that provides information when the probe is moved proximate to the at least one marker.

8. A system for identifying, stabilizing and removing a tissue volume comprising:

a. a marker system including:
  i. at least one marker having a maximum dimension of no more than 5 mm, as measured along any axis extending through the at least one marker;
  ii. a probe; and
  iii. a detector connected to the probe that provides information when the probe is moved proximate to at least one marker;

b. a cutter including:
  i. a first portion having:
    (1) a first blade having a first edge with a first curved configuration;
    (2) a first connector;
  ii. a second portion having:
    (1) a second blade having a second edge, wherein the second edge has a second curved configuration that is designed so that when the second blade is positioned in operative engagement with the first blade, the first edge and the second edge form a substantially continuous cutting edge;
    (2) a second connector positioned and designed to releasably engage the first connector to releasably secure the second blade in the operative engagement with the first blade; and c. a tissue anchor including:
  i. an elongate tube having a central bore, a distal end and a proximal end, wherein the tube has at least one aperture adjacent the distal end;
  ii. an elongate member having a portion sized for receipt and axial movement in the central bore between a first position and a second position, wherein the elongate member includes a longitudinal axis and at least one anchor member attached to the portion; and
  iii. wherein the at least one anchor member is configured and positioned so that when the portion is in the first position the at least one anchor member is at least partially received in the elongate tube and when the portion is in the second position the at least one anchor member projects through the at least one aperture and extends transversely relative to the longitudinal axis.

9. A method of removing a tissue mass and surrounding tissue volume from a piece of tissue, the method comprising the steps:

a. positioning at least one marker in the piece of tissue so as to define a boundary of the tissue volume;

b. identifying the boundary by detecting the position of the at least one marker;

c. incising portions of the tissue volume adjacent the at least one marker substantially along the boundary based on the position of the at least one marker; and d. stabilizing the tissue volume during the incising step;

wherein the identifying step and incising step are repeated until the tissue volume is removed from the piece of tissue.

10. A method of removing a tissue mass and surrounding tissue volume from a piece of tissue, the method comprising the steps;

a. positioning at least one marker in the piece of tissue so as to define a boundary of the tissue volume;

b. identifying the boundary by detecting the position of the at least one marker;

c. incising portions of the tissue volume adjacent the at least one marker substantially along the boundary based on the position of the at least one marker; and d. stabilizing the tissue volume during the incising step by pulling the tissue volume in a first direction;

wherein the incising step is performed so that the incising extends in a second direction that is different than the first direction.

11. A method for removing a tissue mass and surrounding tissue volume from a piece of tissue, the method comprising the steps:

a. positioning at least one marker in the piece of tissue so as to define a boundary of the tissue volume;

b. identifying the boundary by detecting the position of the at least one marker;

c. incising portions of the tissue volume adjacent the at least one marker substantially along the boundary based on the position of the at least one marker; and d. stabilizing the tissue volume during the incising step;

wherein the stabilizing step involves pulling the tissue volume in a first direction.

12. A method, of removing a tissue volume from a tissue portion using at least one marker, the method comprising the steps:

a. positioning at least one marker so as to define a boundary of the tissue volume wherein said at least one marker comprises a plurality of markers, and wherein positioning the at least one marker comprises positioning a plurality of the markers in the tissue volume;

b. detecting the locations of the plurality of markers; and c. incising portions of the tissue portion adjacent the at least one marker substantially along the boundary adjacent the location.

13. A method according to claim 12, wherein the positioning step is performed so that the plurality of markers define the boundary in three dimensions.

14. A method according to claim 12, wherein the positioning step is performed so that the plurality of markers define the boundary in two dimensions.

15. A method according to claim 12, wherein the positioning step is performed so that the plurality of markers define the boundary in one dimension.

16. A method according to claim 12, wherein the plurality of markers includes three pairs of markers, further wherein the positioning step involves positioning the three pairs of markers so that markers of each pair lie on the boundary in mutually spaced relation substantially on opposite sides of the tissue volume.

17. A method according to claim 12, wherein the positioning step involves positioning the plurality of markers so that at least two of the plurality of markers lie on an X axis and at least two of the plurality of markers lie on a Y axis, wherein the X axis and the Y axis intersect the tissue volume and extend in non-coaxial relation.

18. A method according to claim 12, further including the steps of repeating the detecting step and the incising step with respect to other ones of the plurality of markers.

19. A method according to claim 12, further including the steps of repeating the detecting step and the incising step with respect to all of the plurality of markers until the tissue volume is separated from the tissue portion.

20. A method of bracketing a tissue mass in a piece of tissue using a least one marker, the method comprising the steps:

a. generating an image of the tissue mass;

b. referring to the image of the tissue mass and positioning a plurality of markers in the piece of tissue so as to define the boundary of the tissue volume; and c. locating the markers using a device that provides information when the device is moved proximate to at least one of the markers.

21. A method according to claim 20, wherein the step b involves positioning the plurality of markers so that two of the plurality of markers are positioned on an X axis, two of the plurality of markers are positioned on a Y axis and two of the plurality of markers are positioned on a Z axes, the X, Y and Z axes intersecting the tissue volume and extending in non-coplanar relation.

22. A method according to claim 20, wherein the step b involves positioning the plurality of markers so that the X, Y and Z axes are substantially mutually orthogonal.

23. A method according to claim 20, wherein the step b is performed so that the plurality of markers defines the boundary in one dimension.

24. A method according to claim 20, wherein the step b is performed so that the plurality of markers define the boundary in two dimensions.

25. A method according to claim 20, wherein the step b is performed so that the plurality of markers defines the boundary in three dimensions.

26. A method according to claim 20, wherein the step b is performed so that the at least two of the plurality of markers are positioned on an $X_1$ axis and at least two of the plurality of markers ate positioned on a $Y_1$ axis, wherein the $X_1$ axis and the $Y_1$ axis are offset along the Z axis, respectively, from the X axis and the Y axis.

* * * * *

UNITED STATES PATENT AND TRADEMARK OFFICE
CERTIFICATE OF CORRECTION

PATENT NO. : 6,363,940 B1 Page 1 of 1
DATED : April 2, 2002
INVENTOR(S) : David N. Krag It is certified that error appears in the above-identified patent and that said Letters Patent is hereby corrected as shown below:

<u>Title page,</u>
Item [56], References Cited, FOREIGN PATENT DOCUMENTS, "WO 9608208 A1" should be -- WO 96/08208 A1 --;

<u>Column 6,</u>
Line 15, "microCurries" should be -- microcuries --;

<u>Column 17,</u>
Line 15, "makers" should be -- markers --;

<u>Column 18,</u>
Line 6-7, insert -- or -- after "location";

<u>Column 24,</u>
Line 36, semicolon should be colon;
Line 49, "for" should be -- of --;
Line 63, delete the comma;
Line 57, "said" should be -- the --;

<u>Column 26,</u>
Line 2, "a" should be -- at --;
Line 14, "axes" should be -- axis --;
Line 32, "ate" should be -- are --.

Signed and Sealed this

Sixteenth Day of December, 2003

JAMES E. ROGAN
*Director of the United States Patent and Trademark Office*